US012648696B2

(12) United States Patent
Bowden et al.

(10) Patent No.: US 12,648,696 B2
(45) Date of Patent: Jun. 9, 2026

(54) SYSTEMS FOR NEUROIMAGER ALIGNMENT AND COUPLING EVALUATION

(71) Applicants: Vanderbilt University, Nashville, TN (US); The Board of Trustees of the Leland Stanford Junior University, Stanford, CA (US)

(72) Inventors: Audrey K. Bowden, Nashville, TN (US); Seyed M Hadi Hosseini, San Carlo, CA (US); Anupam Kumar, Nashville, TN (US)

(73) Assignees: Vanderbilt University, Nashville, TN (US); The Board of Trustees of the Leland Stanford Junior University, Stanford, CA (US)

( * ) Notice: Subject to any disclaimer, the term of this patent is extended or adjusted under 35 U.S.C. 154(b) by 236 days.

(21) Appl. No.: 18/194,560

(22) Filed: Mar. 31, 2023

(65) Prior Publication Data

US 2023/0337919 A1     Oct. 26, 2023

Related U.S. Application Data

(60) Provisional application No. 63/326,192, filed on Mar. 31, 2022.

(51) Int. Cl.
| | |
|---|---|
| *A61B 5/00* | (2006.01) |
| *A61B 90/00* | (2016.01) |
| *G06T 7/00* | (2017.01) |

(52) U.S. Cl.
CPC .......... *A61B 5/0042* (2013.01); *A61B 5/0075* (2013.01); *A61B 5/4064* (2013.01);
(Continued)

(58) Field of Classification Search
CPC ............ A61B 2090/365; A61B 5/0042; A61B 5/0075; A61B 5/4064; A61B 5/6803;
(Continued)

(56) References Cited

U.S. PATENT DOCUMENTS

| | | | | |
|---|---|---|---|---|
| 10,795,440 B1 * | 10/2020 | Chevillet | ............ | G06F 18/2413 |
| 11,100,636 B2 * | 8/2021 | Yu | .......................... | A61B 5/721 |

(Continued)

FOREIGN PATENT DOCUMENTS

| | | |
|---|---|---|
| AU | 2012298253 A1 | 4/2014 |
| CA | 2887361 A1 | 4/2014 |

(Continued)

OTHER PUBLICATIONS

Khan B., Wildey C., Francis R., Tian F., Delgado M.R., Liu H., Macfarlane D., Alexandrakis G. Improving optical contact for functional near-infrared brain spectroscopy and imaging with brush optodes. Biomed. Opt. Express. 2012;3:878-898.

(Continued)

*Primary Examiner* — Ming Wu
(74) *Attorney, Agent, or Firm* — Michael Best & Friedrich LLP

(57)     ABSTRACT

In an embodiment, a neuroimager alignment and coupling evaluation (NACE) system, includes a neuroimaging device; a fiducial affixed to the neuroimaging device; an imaging device; and an augmented reality (AR) module coupled to the imaging device and configured to provide alignment data for the neuroimaging device by tracking facial or cranial landmarks and the fiducial.

14 Claims, 12 Drawing Sheets

(52) U.S. Cl.
CPC ................. *A61B 90/36* (2016.02); *G06T 7/00* (2013.01); *A61B 2090/365* (2016.02); *G06T 2207/30201* (2013.01)

(58) Field of Classification Search
CPC ......... A61B 90/36; G01S 19/01; G01S 19/42; G01S 2205/01; G01S 5/0027; G01S 5/14; G06Q 10/0833; G06Q 10/087; G06T 2207/30201; G06T 2207/30204; G06T 2207/30244; G06T 7/00; G06T 7/33
See application file for complete search history.

(56) References Cited

U.S. PATENT DOCUMENTS

| | | | |
|---|---|---|---|
| 2015/0055137 A1 | 2/2015 | Brown et al. | |
| 2017/0293121 A1 | 10/2017 | Kawamura | |
| 2018/0027159 A1 | 1/2018 | Dillon et al. | |
| 2019/0229558 A1* | 7/2019 | Pigeon | A61N 1/3787 |
| 2020/0138518 A1* | 5/2020 | Lang | A61B 17/1703 |
| 2021/0186330 A1* | 6/2021 | Hall | A61B 5/6803 |
| 2022/0015629 A1 | 1/2022 | Seibel et al. | |
| 2022/0256088 A1 | 8/2022 | Bloch et al. | |
| 2022/0282954 A1 | 9/2022 | Volkov | |
| 2022/0357584 A1 | 11/2022 | Eggleston et al. | |
| 2022/0365336 A1 | 11/2022 | Samanta et al. | |
| 2023/0024072 A1 | 1/2023 | Ji et al. | |
| 2023/0314123 A1 | 10/2023 | Bowden | |
| 2024/0032827 A1 | 2/2024 | Durr et al. | |
| 2024/0203101 A1 | 6/2024 | Zhang et al. | |

FOREIGN PATENT DOCUMENTS

| | | |
|---|---|---|
| CA | 3238125 A1 | 12/2018 |
| CA | 3092259 A1 | 9/2019 |
| CA | 3100265 A1 | 10/2020 |
| CA | 3165710 A1 | 7/2021 |
| CA | 3234191 A1 | 5/2023 |
| CN | 110742575 A | 2/2020 |
| CN | 211426245 U | 9/2020 |
| CN | 112545449 A | 3/2021 |
| DE | 102016121246 A1 | 5/2018 |
| EP | 3757648 A1 | 12/2020 |
| WO | 2010/009450 A1 | 1/2010 |
| WO | 2014/048573 A1 | 4/2014 |
| WO | 2015/168157 A1 | 11/2015 |
| WO | 2019/222616 A1 | 11/2019 |
| WO | 2023/165081 A1 | 9/2023 |

OTHER PUBLICATIONS

Kight, Emily, Iftak Hussain, and Audrey K. Bowden. "Low-cost, volume-controlled dipstick urinalysis for home-testing." JoVE (Journal of Visualized Experiments) 171 (2021): e61406.

Kim CK, Lee S, Koh D, Kim BM. Development of wireless NIRS system with dynamic removal of motion artifacts. Biomed Eng Lett. 2011;1(4):254-259.

Kim, Sanghoon, et al. "Design and implementation of a low-cost, portable OCT system." Biomedical optics express 9.3 (2018): 1232-1243.

Kumar, Anupam, et al. "User-centric hardware and software development for low-cost naturalistic neuroimaging using fNIRS." Optical Tomography and Spectroscopy. Optica Publishing Group, 2022, 2 pages.

Kurz E.M., Wood G., Kober S.E., Schippinger W., Pichler G., Müller-Putz G., Bauernfeind G. Towards using fNIRS recordings of mental arithmetic for the detection of residual cognitive activity in patients with disorders of consciousness (DOC) Brain Cogn. 2018;125:78-87.

Landowska A, Royle S, Eachus P, Roberts D. Testing the Potential of Combining Functional Near-Infrared Spectroscopy with Different Virtual Reality Displays-Oculus Rift and oCtAVE. In: Jung, T and Dieck M, ed. Augmented Reality and Virtual Reality: Empowering Human, Place and Business. Progress in IS. ; 2018:309-321.

Lange F., Dunne L., Hale L., Tachtsidis I. Maestros: a multiwavelength time-domain NIRS system to monitor changes in oxygenation and oxidation state of cytochrome-C-oxidase. IEEE J. Sel. Top. Quantum Electron. 2019;25.

Lee, Kyung Chul, et al. "A smartphone-based Fourier ptychographic microscope using the display screen for illumination." ACS Photonics 8.5 (2021): 1307-1315.

Liu Y., Ayaz H. Speech recognition via fNIRS based brain signals. Front. Neurosci. 2018;12.

Machado A, Cai Z, Pellegrino G, et al. Optimal positioning of optodes on the scalp for personalized functional near-infrared spectroscopy investigations. J Neurosci Methods. 2018;309(Nov. 2017):91-108.

Malone, Joseph D., et al. "DiffuserSpec: spectroscopy with Scotch tape." Optics Letters 48.2 (2023): 323-326.

McGreevey, S. Finding signs of life when it matters most. The Harvard Gazette. Jul. 20, 2017. Available online at https://news.harvard.edu/gazette/story/2017/07/using-fmri-eeg-to-search-for-consciousness-in-icu-patients/ (3 pages).

McKendrick R., Mehta R., Ayaz H., Scheldrup M., Parasuraman R. Prefrontal hemodynamics of physical activity and environmental complexity during cognitive work. Hum. Factors. 2017;59(1):147-162.

Mehta, Rajvi, et al. "Wireless, web-based interactive control of optical coherence tomography with mobile devices." Translational Vision Science & Technology 6.1 (2017): 5-5.

Meng, Xin, et al. "Smartphone based hand-held quantitative phase microscope using the transport of intensity equation method." Lab on a Chip 17.1 (2017): 104-109.

Merzagora A.C., Schultheis M.T., Onaral B., Izzetoglu M. Functional near-infrared spectroscopy-based assessment of attention impairments after traumatic brain injury. J. Innov. Opt. Health Sci. 2011;04(03):251-260.

Mihajlovic V, Grundlehner B, Vullers R, Penders J. Wearable, wireless EEG solutions in daily life applications: What are we missing? IEEE J Biomed Heal Informatics. 2015;19(1):6-21.

Mihajlovic V, Patki S, Xu J. Noninvasive Wearable Brain Sensing. In: IEEE Sensors Journal. vol 18. IEEE Sensors. ; 2017:1661-1663.

Morikawa, Chamin, et al. "Image and video processing on mobile devices: a survey." The Visual Computer 37.12 (2021): 2931-2949.

Moshiri, Yasman, et al. "Handheld swept-source optical coherence tomography with angiography in awake premature neonates." Quantitative Imaging in Medicine and Surgery 9.9 (2019): 1495.

Murphy K., Harris A.D., Wise R.G. Robustly measuring vascular reactivity differences with breath-hold: normalising stimulus-evoked and resting state BOLD fMRI data. Neuroimage. 2011;54:369-379.

Nakamura, Yoshifumi, et al. "High-speed three-dimensional human retinal imaging by line-field spectral domain optical coherence tomography." Optics express 15.12 (2007): 7103-7116.

NewmanBrain. fNIR BrainSpy 28, (n.d.). Version dated Jan. 24, 2022. Available online at https://web.archive.org/web/20220124232555/https://www.newmanbrain.com/fnir-brainspy-28/ (5 pages).

NPS Medicinewise. Antibiotics, explained. Version accessed on Mar. 23, 2022. Retrieved from https://web.archive.org/web/20220323102023/https://www.nps.org.au/consumers/antibiotics-explained (4 pages).

Obelab. Nirsit Operator's Manual, 2016 (45 pages).

Obelab. Nirsit-Lite Kids Brain Imaging System for Kids. Brochure. 2020. Available online at http://obelab.com/upload_file/down/Nirsit-Lite(kids)Brochure-research(eng2020).pdf (2 pages).

Obrig H. NIRS in clinical neurology a 'promising' tool? Neuroimage. 2014;85:535-546.

Obrig, Hellmuth, et al. "Near-infrared spectroscopy: does it function in functional activation studies of the adult brain?." International Journal of Psychophysiology 35.2-3 (2000): 125-142.0.

Pfeifer M.D., Scholkmann F., Labruyère R. Signal processing in functional near-infrared spectroscopy (fNIRS): methodological differences lead to different statistical results. Front. Hum. Neurosci. 2018;11:1-12.

(56)          References Cited

OTHER PUBLICATIONS

Pi, Shaohua, et al. "Imaging retinal structures at cellular-level resolution by visible-light optical coherence tomography." Optics letters 45.7 (2020): 2107-2110.

Pinti P, Aichelburg C, Gilbert S, et al. A Review on the Use of Wearable Functional Near-Infrared Spectroscopy in Naturalistic Environments. Jpn Psychol Res. 2018;60(4):347-373.

Pollonini L, Bortfeld H, Oghalai JS. Phoebe: a method for real time mapping of optodes-scalp coupling in functional near-infrared spectroscopy. Biomed Opt Express. 2016;7(12):5104.

Potter, L. Urinalysis—OSCE Guide. Version accessed Mar. 24, 2022, available online at https://web.archive.org/web/20220324195636/http://geekymedics.com/urinalysis-osce-guide/ (43 pages).

Quaresima V., Ferrari M. Functional Near-Infrared Spectroscopy (fNIRS) for assessing cerebral cortex function during human behavior in natural/social situations: a concise review. Organ. Res. Methods. 2019;22(1):46-68.

Rao, Adrit, and Harvey A. Fishman. "OCTAI: Smartphone-based Optical Coherence Tomography Image Analysis System." 2021 IEEE World AI IoT Congress (AIIoT). IEEE, 2021.

Romero-Ramirez, F.J. et al. Speeded up detection of squared fiducial markers, Image Vis. Comput. 76 (2018) 38-47.

Roy, Somak, et al. "Smartphone adapters for digital photomicrography." Journal of pathology informatics 5.1 (2014): 24.

Safaie J, Grebe R, Moghaddam HA, Wallois F. Toward a fully integrated wireless wearable EEG-NIRS bimodal acquisition system. J Neural Eng. 2013;10(5).

Saikia MJ, Besio WG, Mankodiya K. WearLight: Toward a Wearable, Configurable Functional NIR Spectroscopy System for Noninvasive Neuroimaging. IEEE Trans Biomed Circuits Syst. 2019; 13(1):91-102.

Samsung. ISOCELL 2L4 Specifications. Version accessed on Nov. 2, 2021. Available oonline at https://web.archive.org/web/20211102045607/https://www.samsung.com/semiconductor/minisite/isocell/mobile-image-sensors/isocell-fast-214/ (8 pages).

Sappia, M.S. et al. Signal quality index: an algorithm for quantitative assessment of functional near infrared spectroscopy signal quality, Biomed. Opt. Express. 11 (2020) 6732.

Sato T. et al. Reduction of global interference of scalp-hemodynamics in functional near-infrared spectroscopy using short distance probes. Neuroimage. 2016;141:120-132.

Science of Psychotherapy. Prefontal Cortex webpage. Jan. 4, 2017. Version accessed Feb. 19, 2022. Available online at: https://www.thescienceofpsychotherapy.com/prefrontal-cortex/ (24 pages).

Shu, Xiao, et al. "Designing visible-light optical coherence tomography towards clinics." Quantitative Imaging in Medicine and Surgery 9.5 (2019): 769.

Si, Juanning, et al. "A portable fNIRS system with eight channels." Optical techniques in neurosurgery, neurophotonics, and optogenetics II. vol. 9305. SPIE, 2015.

Smith, G. T., et al. "Low-power, low-cost urinalysis system with integrated dipstick evaluation and microscopic analysis." Lab on a Chip 18.14 (2018): 2111-2123.

Smith, G. T., et al. "Robust dipstick urinalysis using a low-cost, micro-vol. slipping manifold and mobile phone platform." Lab on a Chip 16.11 (2016): 2069-2078.

Smith, K. Urinalysis: How the Test Is Done and What Results Mean | Everyday Health. Version accessed Mar. 9, 2022, available online at https://web.archive.org/web/20220309073835/https://www.everydayhealth.com/urine/urinalysis-how-test-done-what-results-mean/ (14 pages).

Soetikno, Brian T., et al. "Inner retinal oxygen metabolism in the 50/10 oxygen-induced retinopathy model." Scientific reports 5.1 (2015): 1-14.

Almajidy R.K., Hofmann U.G. On the design of a multi-channel NIR system to monitor functional brain activity. NIR2013 Proc. 2013:335-338.

Arganda-Carreras, Ignacio, Carlos OS Sorzano, Roberto Marabini, José María Carazo, Carlos Ortiz-de-Solorzano, and Jan Kybic. "Consistent and elastic registration of histological sections using vector-spline regularization." In Computer Vision Approaches to Medical Image Analysis: Second International ECCV Workshop, CVAMIA 2006 Graz, Austria, May 12, 2006 Revised Papers 2, pp. 85-95. Springer Berlin Heidelberg, 2006.

Artemenko C., Soltanlou M., Ehlis A.C., Nuerk H.C., Dresler T. The neural correlates of mental arithmetic in adolescents: a longitudinal fNIRS study. Behav. Brain Funct. 2018;14:1-13.

Atsumori H., Kiguchi M., Katura T., Funane T., Obata A., Sato H., Manaka T., Iwamoto M., Maki A., Koizumi H., Kubota K. Noninvasive imaging of prefrontal activation during attention-demanding tasks performed while walking using a wearable optical topography system. J. Biomed. Opt. 2010;15.

Bale G., Elwell C.E., Tachtsidis I. From Jöbsis to the present day: a review of clinical near-infrared spectroscopy measurements of cerebral cytochrome-c-oxidase. J. Biomed. Opt. 2016;21.

Beauchamp, M. S., et al. "The developmental trajectory of brain-scalp distance from birth through childhood: implications for functional neuroimaging." PloS one 6.9 (2011): e24981.

Bellina, Livia, and Eduardo Missoni. "Mobile cell-phones (M-phones) in telemicroscopy: increasing connectivity of isolated laboratories." Diagnostic pathology 4 (2009): 1-4.

Bhutta M.R., Hong K.S., Kim B.M., Hong M.J., Kim Y.H., Lee S.H. Note: three wavelengths near-infrared spectroscopy system for compensating the light absorbance by water. Rev. Sci. Instrum. 2014;85:2012-2015.

Blahnik, Vladan, and Oliver Schindelbeck. "Smartphone imaging technology and its applications." Advanced Optical Technologies 10.3 (2021): 145-232.

Breslauer, David N., et al. "Mobile phone based clinical microscopy for global health applications." PloS one 4.7 (2009): e6320.

Burggraaff, O., Schmidt, N., Zamorano, J., Pauly, K., Pascual, S., Tapia, C., Spyrakos, E. and Snik, F., 2019. Standardized spectral and radiometric calibration of consumer cameras. Optics express, 27(14), pp. 19075-19101.

Cavalcanti, Thiago C., et al. "Smartphone-based spectral imaging otoscope: System development and preliminary study for evaluation of its potential as a mobile diagnostic tool." Journal of Biophotonics 13.6 (2020): e2452.

Chénier F, Sawan M. A new brain imaging device based on fNIRS. Conf Proc—IEEE Biomed Circuits Syst Conf Healthc Technol BiOCAS2007. 2007;(Dec.):1-4.

Chiarelli AM, Zappasodi F, di Pompeo F, et al. Flexible CW-fNIRS system based on Silicon Photomultipliers: In-Vivo characterization of sensorimotor response. In: 2017 IEEE Sensors. IEEE Sensors. ; 2017:1673-1675.

Chong, S.P., Bernucci, M., Radhakrishnan, H. and Srinivasan, V.J., 2017. Structural and functional human retinal imaging with a fiber-based visible light OCT ophthalmoscope. Biomedical optics express, 8(1), pp. 323-337.

Chong, Shau Poh, et al. "Ultrahigh resolution retinal imaging by visible light OCT with longitudinal achromatization." Biomedical optics express 9.4 (2018): 1477-1491.

Curtin A, Ayaz H. The Age of Neuroergonomics: Towards Ubiquitous and Continuous Measurement of Brain Function with fNIRS. Jpn Psychol Res. 2018;60(4, SI):374-386.

Dai, Bo, et al. "Colour compound lenses for a portable fluorescence microscope." Light: Science & Applications 8.1 (2019): 75.

Dempsey L.A., Cooper R.J., Roque T., Correia T., Magee E., Powell S., Gibson A.P., Hebden J.C. Data-driven approach to optimum wavelength selection for diffuse optical imaging. J. Biomed. Opt. 2015;20.

Dravida S, Ono Y, Noah JA, Zhang X, Hirsch J. Co-localization of theta-band activity and hemodynamic responses during face perception: simultaneous electroencephalography and functional near-infrared spectroscopy recordings. Neurophotonics. 2019;6(04):1.

Dsouza, Roshan, et al. "Economical and compact briefcase spectral-domain optical coherence tomography system for primary care and point-of-care applications." Journal of biomedical optics 23.9 (2018): 096003-096003.

Ellerbee, Audrey K., et al. "Quantifying colorimetric assays in paper-based microfluidic devices by measuring the transmission of light through paper." Analytical chemistry 81.20 (2009): 8447-8452.

(56) References Cited

OTHER PUBLICATIONS

Falk TH, Guirgis M, Power S, Chau TT. Taking NIRS-BCIs outside the lab: Towards achieving robustness against environment noise. IEEE Trans Neural Syst Rehabil Eng. 2011;19(2):136-146.

Fechtig, Daniel J., et al. "Line-field parallel swept source interferometric imaging at up to 1 MHz." Optics Letters 39.18 (2014): 5333-5336.

Freeman, Esther E., et al. "Smartphone confocal microscopy for imaging cellular structures in human skin in vivo." Biomedical optics express 9.4 (2018): 1906-1915.

Funane, Tsukasa, et al. "Noncontact brain activity measurement system based on near-infrared spectroscopy." Applied Physics Letters 96.12 (2010): 123701.

Ga L., Yucel M., Boas D., Cooper R. Further improvement in reducing superficial contamination in NIRS using double short separation measurements. Bone. 2008;23:1-7.

Gagnon L., Perdue K., Greve D.N., Goldenholz D., Kaskhedikar G., Boas D.A. Improved recovery of the hemodynamic response in diffuse optical imaging using short optode separations and state-space modeling. Neuroimage. 2011;56 (3):1362-1371.

Gagnon Louis, Cooper Robert J., Yücel Meryem A., Perdue Katherine L., Greve Douglas N., Boas David A. Short separation channel location impacts the performance of short channel regression in NIRS. Neuroimage. 2012;59 (3):2518-2528.

Garrido-Jurado S, Muñoz-Salinas R, Madrid-Cuevas FJ, Medina-Carnicer R. Generation of fiducial marker dictionaries using Mixed Integer Linear Programming. Pattern Recognit. 2016;51(Oct.):481-491.

Ge S, Yang Q, Wang R, et al. A Brain-Computer Interface Based on a Few-Channel EEG-fNIRS Bimodal System. IEEE Access. 2017;5:208-218.

Glasser MF, Coalson TS, Robinson EC, et al. A multi-modal parcellation of human cerebral cortex. Nature. 2017;536 (7615):171-178.

Hamilton, Antonia, et al. "Seeing into the brain of an actor with mocap and fNIRS." Proceedings of the 2018 ACM International Symposium on Wearable Computers. 2018.

Han, Le, et al. "Line-scanning SD-OCT for in-vivo, non-contact, volumetric, cellular resolution imaging of the human cornea and limbus." Biomedical Optics Express 13.7 (2022): 4007-4020.

He, Bin, et al. "Electrophysiological imaging of brain activity and connectivity—challenges and opportunities." IEEE transactions on biomedical engineering 58.7 (2011): 1918-1931.

He, Qinghua, and Ruikang Wang. "Hyperspectral imaging enabled by an unmodified smartphone for analyzing skin morphological features and monitoring hemodynamics." Biomedical optics express 11.2 (2020): 895-910.

Hirshfield, L.. "6.0 Development of a Remote-fNIRS Device." Version accessed Mar. 2, 2021, available online at https://web.archive.org/web/20210302150053/https://alivelearn.net/wp-content/uploads/2020/05/Leanne_remote_fnirs.pdf (17 pages).

Holtzer, Roee, et al. "fNIRS study of walking and walking while talking in young and old individuals." Journals of Gerontology Series A: Biomedical Sciences and Medical Sciences 66.8 (2011): 879-887.

Homan RW, Herman J, Purdy P. Cerebral location of international 10-20 system electrode placement. Electroencephalogr Clin Neurophysiol. 1987;66(4):376-382.

Huang, Xiwei, et al. "Smartphone-based analytical biosensors." Analyst 143.22 (2018): 5339-5351.

Hunt, B., Ruiz, A.J. and Pogue, B.W., 2021. Smartphone-based imaging systems for medical applications: a critical review. Journal of Biomedical Optics, 26(4), p. 040902.

Hussain, I. and Bowden, A.K., 2021. Smartphone-based optical spectroscopic platforms for biomedical applications: a review. Biomedical Optics Express, 12(4), pp. 1974-1998.

Idelson C.R., Vogt W.C., King-Casas B., LaConte S.M., Rylander C.G. Effect of mechanical optical clearing on near-infrared spectroscopy. Lasers Surg. Med. 2015;47:495-502.

Izzetoglu, K. et al. "Functional near-infrared neuroimaging," The 26th Annual International Conference of the IEEE Engineering in Medicine and Biology Society, San Francisco, CA, USA, 2004, pp. 5333-5336.

Jaffe-Dax S, Bermano AH, Erel Y, Emberson LL. Video-based motion-resilient reconstruction of three-dimensional position for functional near-infrared spectroscopy and electroencephalography head mounted probes. Neurophotonics. 2020;7(03):1.

Jasińska KK, Guei S. Neuroimaging field methods using functional near infrared spectroscopy (NIRS) neuroimaging to study global child development: Rural sub-Saharan Africa. J Vis Exp. 2018;2018(132):1-11.

Jurcak V, Tsuzuki D, Dan I. 10/20, 10/10, and 10/5 systems revisited: Their validity as relative head-surface-based positioning systems. Neuroimage. 2007;34(4):1600-1611.

Kassab A, Le Lan J, Tremblay J, et al. Multichannel wearable fNIRS-EEG system for long-term clinical monitoring. Hum Brain Mapp. 2018;39(1):7-23.

Kawaguchi H, Yamada T. A fNIRS probe positioning system using augmented reality technology. In: SPIE-Intl Soc Optical Eng; 2019:53.

Kazemi, V. et al. One millisecond face alignment with an ensemble of regression trees, Proc. IEEE Comput. Soc. Conf. Comput. Vis. Pattern Recognit. (2014) 1867-1874.

Song C, Jeon S, Lee S, Ha HG, Kim J, Hong J. Augmented reality-based electrode guidance system for reliable electroencephalography. Biomed Eng Online. 2018;17(1).

Song, Ge, et al. "First clinical application of low-cost OCT." Translational vision science & technology 8.3 (2019): 61-61.

Statista. "Smartphone subscriptions worldwide 2027 | Statista." Version accesssed Mar. 20, 2022. Available online at https://web.archive.org/web/20220320015240/https://www.statista.com/statistics/330695/number-of-smartphone-users-worldwide/ (2 pages).

Stillman A.E., Hu X., Jerosch-Herold M. Functional MRI of brain during breath holding at 4 T. Magn. Reson. Imaging. 1995;13(6):893-897.

Strangman G.E., Li Z., Zhang Q. Depth sensitivity and source-detector separations for near infrared spectroscopy based on the Colin27 brain template. PLoS One. 2013;8.

Sumner, Rob. "Processing raw images in matlab." Department of Electrical Engineering, University of California Sata Cruz 2 (2014).

Surre, Jérémy, et al. "Strong increase in the autofluorescence of cells signals struggle for survival." Scientific reports 8.1 (2018): 1-14.

Switz, Neil A., Michael V. D'Ambrosio, and Daniel A. Fletcher. "Low-cost mobile phone microscopy with a reversed mobile phone camera lens." PloS one 9.5 (2014): e95330.

Tamnes, Christian K., et al. "Development of the cerebral cortex across adolescence: a multisample study of inter-related longitudinal changes in cortical volume, surface area, and thickness." Journal of Neuroscience 37.12 (2017): 3402-3412.

Tankeshwar, A. Mueller Hinton Agar (MHA): Composition, preparation and uses. Jul. 20, 2013. Version accessed May 9, 2021, Retrieved from https://web.archive.org/web/20210509170120/https://microbeonline.com/why-mueller-hinton-agar-is-used-in-routine-antibiotic-susceptibility-testing/ (3 pages).

Teichman, Joshua C., Kashif Baig, and Iqbal Ike K. Ahmed. "Simple technique to measure toric intraocular lens alignment and stability using a smartphone." Journal of Cataract & Refractive Surgery 40.12 (2014): 1949-1952.

Teranaka, Hayato, et al. "Single-sensor RGB and NIR image acquisition: toward optimal performance by taking account of CFA pattern, demosaicking, and color correction." Electronic Imaging 2016.18 (2016): 1-6.

Thomason Moriah E., Burrows Brittany E., Gabrieli John D.E., Glover Gary H. Breath holding reveals differences in fMRI BOLD signal in children and adults. Neuroimage. 2005;25(3):824-837.

Tsow F., et al. Wearable Functional Near-Infrared (FNIR) Technology and Its Applications in Naturalistic Conditions, Am J Biomed Sci & Res. 2019-5(1). AJBSR.MS.ID.000869.

Tsow, Francis, et al. "A low-cost, wearable, do-it-yourself functional near-infrared spectroscopy (DIY-fNIRS) headband." HardwareX 10 (2021): e00204.

(56) References Cited

OTHER PUBLICATIONS

Uthoff, Ross D., et al. "Point-of-care, multispectral, smartphone-based dermascopes for dermal lesion screening and erythema monitoring." Journal of biomedical optics 25.6 (2020): 066004.

Von Lühmann A., Herff C., Heger D., Schultz T. Toward a wireless open source instrument: functional near-infrared spectroscopy in mobile neuroergonomics and BCI applications. Front. Hum. Neurosci. 2015;9:617.

Von Lühmann A., Wabnitz H., Sander T., Müller K. M3BA: a mobile, modular, multimodal biosignal acquisition architecture for miniaturized EEG-NIRS-based hybrid BCI and monitoring. IEEE Trans. Biomed. Eng. 2017;64:1199-1210.

Wang, Y. and Liu, X., 2021. Line field Fourier domain optical coherence tomography based on a spatial light modulator. Applied Optics, 60(4), pp. 985-992.

Wojtkowski, Maciej, et al. "Ultrahigh-resolution, high-speed, Fourier domain optical coherence tomography and methods for dispersion compensation." Optics express 12.11 (2004): 2404-2422.

World Health Organization. Causes of Antibiotic Resistance infographic. Version accessed Sep. 1, 2018. Available online at https://web.archive.org/web/20180901000034/https://www.phpnepal.org.np/images/PUBLICATION-NEWS/Global-Health/Causes-antibiotic-resistance.jpg (1 pages).

Wyser D., Lambercy O., Scholkmann F., Wolf M., Gassert R. Wearable and modular functional near-infrared spectroscopy instrument with multidistance measurements at four wavelengths. Neurophotonics. 2017;4.

Xing, Fangjian, et al. "Design and optimization of line-field optical coherence tomography at visible wavebands." Biomedical Optics Express 12.3 (2021): 1351-1365.

Yamada T., Umeyama S., Kamoshida A. Method for leveling the signal-to-noise ratio in multichannel functional near-infrared spectroscopy. Proc. SPIE. 2017.

Yaqub M. Atif, Woo Seong-Woo, Hong Keum-Shik. Compact, portable, high-density functional near-infrared spectroscopy system for brain imaging. IEEE Access. 2020;8:128224-128238.

Yi, Ji, et al. "Human retinal imaging using visible-light optical coherence tomography guided by scanning laser ophthalmoscopy." Biomedical optics express 6.10 (2015): 3701-3713.

Yücel MA, Lühmann A v., Scholkmann F, et al. Best practices for fNIRS publications. 2021;8(1):012101.

Zhang Q., Yan X., Strangman G.E. Development of motion resistant instrumentation for ambulatory near-infrared spectroscopy. J. Biomed. Opt. 2011;16:87008.

Zhang, Diming, and Qingjun Liu. "Biosensors and bioelectronics on smartphone for portable biochemical detection." Biosensors and Bioelectronics 75 (2016): 273-284.

Zhao Y., Qiu L., Sun Y., Huang C., Li T. Optimal hemoglobin extinction coefficient data set for near-infrared spectroscopy. Biomed. Opt. Express. 2017;8:5151-5159.

Zhao, H., & Cooper, R. J. (2018). Review of recent progress toward a fiberless, whole-scalp diffuse optical tomography system. Neurophotonics, 5(1), 011012-011012.

Zhou X, Sobczak G, Colette MM, Litovsky RY. Comparing fNIRS signal qualities between approaches with and without short channels. PLoS One. 2021;15(Dec. 12):1-18.

* cited by examiner

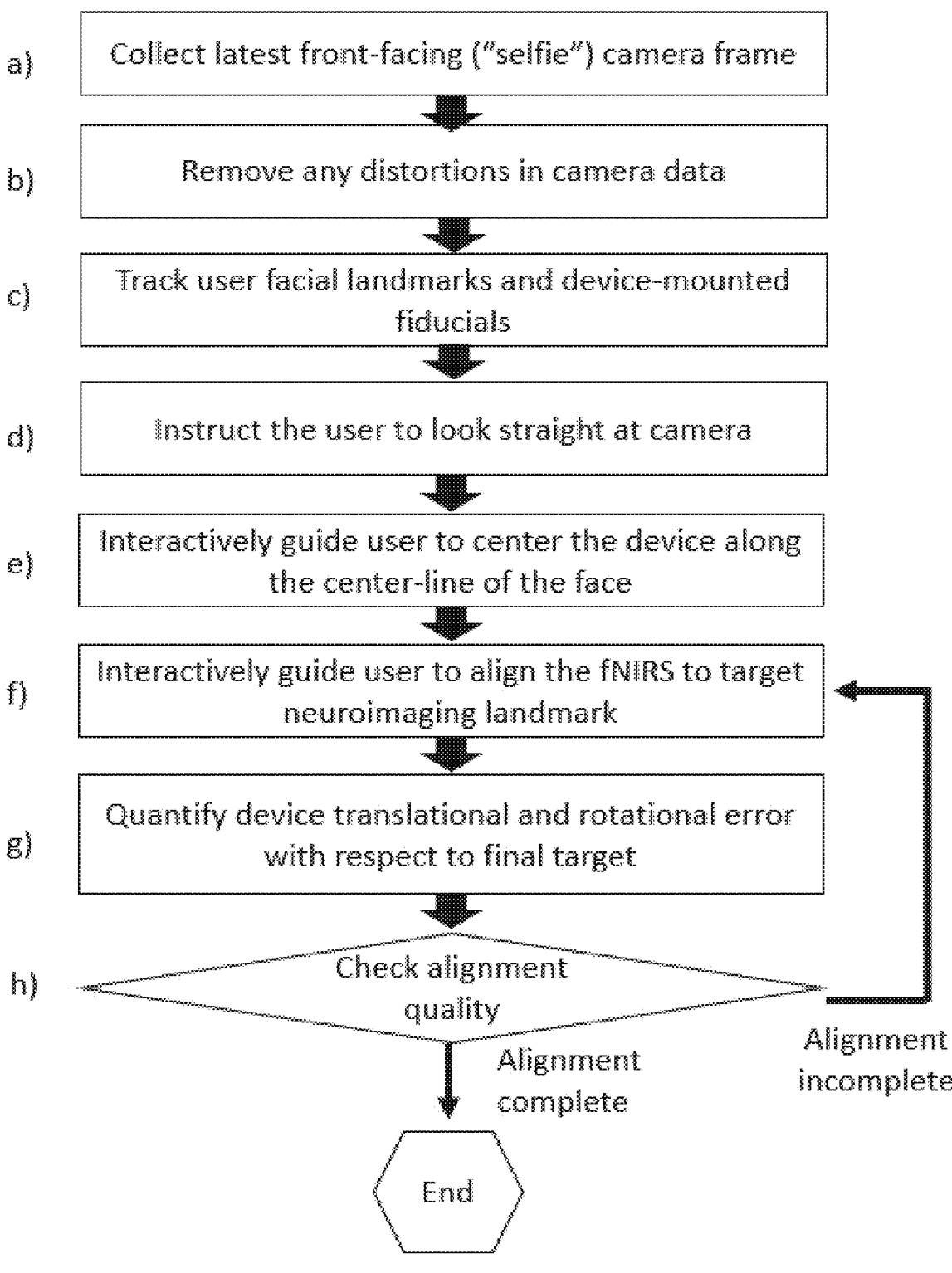

a) Collect latest front-facing ("selfie") camera frame b) Remove any distortions in camera data c) Track user facial landmarks and device-mounted fiducials d) Instruct the user to look straight at camera e) Interactively guide user to center the device along the center-line of the face f) Interactively guide user to align the fNIRS to target neuroimaging landmark g) Quantify device translational and rotational error with respect to final target h) Check alignment quality Alignment complete Alignment incomplete End

FIG. 3B 2D plane

Fiducial corners

Center of fiducial top

Center of fiducial base

Right/left eyebrow apex

Center of eyebrow line

Nasion

SYSTEMS FOR NEUROIMAGER ALIGNMENT AND COUPLING EVALUATION

CROSS-REFERENCE TO RELATED APPLICATIONS

This application is a non-provisional of and claims benefit of U.S. Provisional Patent Application No. 63/326,192, filed on Mar. 31, 2022, the entire contents of which are incorporated herein by reference.

STATEMENT REGARDING FEDERALLY SPONSORED RESEARCH OR DEVELOPMENT

This invention was made with Government support under MH123873 awarded by the National Institutes of Health. The Government has certain rights in the invention.

BACKGROUND

Recent studies and meta-analyses have revealed that neuroimaging studies require data from thousands of individuals to overcome the inter-subject variability preventing clinical actionability. In addition to increasing the sample size, naturalistic neuroimaging can also increase the ecological validity of data.

SUMMARY

To meet this requirement, portable neuroimaging in real-world conditions ("naturalistic neuroimaging") such as homes and offices is of increasing interest. Several research and commercial groups have developed ergonomic, portable neuroimaging devices based on functional near-infrared spectroscopy (fNIRS). Many of these devices are designed specifically to image the prefrontal cortex (PFC) region of a user's brain due to absence of hair on foreheads and the significance of executive functioning in cognitive disorders.

Although their portability allows researchers to perform neuroimaging outside laboratories, these systems still require robust procedures to ensure that device sensors are positioned over the same relative forehead locations across multiple subjects. In addition, sensors must be sufficiently coupled to the scalp to yield proper signal quality. Poor sensor placement or scalp coupling can compromise the usability of real-world neuroimaging data and can prevent successful neuroimaging. Moreover, the numerous requirements for successful sensor placement necessitate expert participation and can endanger ambitions for deploying PFC neuroimaging at-scale. There are currently no tools that enable untrained professionals or lay users to place neuroimaging headsets independently when they leave the lab environment.

The standard process for positioning any fNIRS-based systems involves tedious adjustment of caps or enclosures with respect to cranial landmarks (nasion, inion, and pre-auricular points). These landmarks are common cranial features independent of head shape and size that guide the segmentations utilized in the international 10-10 or 10-20 layouts. Identification of the landmarks on a given user's head and subsequent placement of sensors is often a manual process that requires skilled experts to set up each neuroimaging session.

To automate the device placement process for repeated fNIRS neuroimaging, various groups have developed strategies that use expensive three-dimensional (3D) scanning methods such as benchtop digitizers or depth-sensitive infrared cameras to perform a one-time digitization step after probes have been placed on the head. Another group developed a technique to position individual probes using monocular "selfie" cameras that co-register facial-landmark tracking data with high resolution structural MRI scans. Although these techniques allow for fast and reproducible sensor placement across experiments, they require equipment only available in lab environments.

It is important to note that these techniques have been designed specifically to position individual probes of a modular system over a user's head. As a result, 3D scanning data retrieved from various expensive imagers become a necessity.

However, a common feature of many modern neuroimaging systems is that they are not modular and have fixed, unchangeable locations and spacings for their light sources and detectors. Hence, the relative probe positions and inter-probe spacing geometries are known a priori and 3D scanning data may no longer be required.

Importantly, none of the previously developed tools integrate signal quality evaluation into their systems. Real-time signal assessment algorithms have been developed for fNIRS 23,24, but concurrent sensor positioning, and sensor signal quality measurement has not yet been demonstrated.

Accordingly, embodiments of the present disclosure are generally directed to a neuroimager alignment and coupling evaluation (NACE) system. In some embodiments, NACE includes 1) an augmented reality (AR) application (app) for concurrent fNIRS device alignment and signal quality assessment, and 2) a fiducial (e.g., a square ArUCo marker of known size) that is affixed to a Bluetooth-enabled fNIRS device intended for neuroimaging of the prefrontal cortex. In some embodiments, the AR application component of NACE is designed to work with monocular cameras embedded in standard mobile devices across all price categories and provides AR guidance for device placement by tracking landmarks on a user's face and the square fiducial affixed to a Bluetooth-enabled fNIRS device.

Particular embodiments of the subject matter described in this disclosure can be implemented so as to realize one or more of the following advantages. The NACE approach provides an easy-to-adopt, tablet-based solution that allows lay users to self-position fNIRS devices. The system demonstrates that a 2D, monocular camera can be employed for real-time, interactive adjustment of any neuroimaging device. The system also combines both location and signal quality guidance into the same positioning process. The system is easy-to-adopt and does not require specialized equipment for either the researcher or the research subject. It allows quick, independent setup of neuroimaging equipment by lay users and will allow researchers to engage with a larger number of research subjects easily. The technique can be expanded for use with other devices by adding fiducials as needed on other fNIRS device locations.

In one aspect, disclosed herein, are NACE systems. These systems includes a neuroimaging device, a fiducial affixed to the neuroimaging device, an imaging device, and an AR module coupled to the imaging device. The AR module is configured to provide alignment data for the neuroimaging device by tracking facial or cranial landmarks and the fiducial. The AR module is executed by an electronic processor. In some embodiments, the AR module is configured to: receive video data from the imaging device; and process the video data to identify the cranial landmarks and the position of the neuroimaging device. In some embodiments, the systems further includes a user interface. In some embodiments, the AR module is configured to provide the alignment data to the user interface for display. In some embodiments, the alignment data includes AR cues overlaid on a mirrored camera view. In some embodiments, the alignment data quantifies the vertical, lateral, or rotational offset of the neuroimaging device with respect of the cranial landmarks. In some embodiments, the AR module is configured to: receive signal data from the neuroimaging device; determine a measurement of a quality of the signal data; and provide the measurement of the quality of the signal data to the user interface. In some embodiments, the neuroimaging device is an fNIRS device. In some embodiments, the neuroimaging device is affixed to a user and configured to image the PFC region of the user's brain. In some embodiments, the neuroimaging device is Bluetooth-enabled. In some embodiments, the neuroimaging device comprises a light source. In some embodiments, the imaging device comprises a monocular camera embedded in a mobile device. In some embodiments, the fiducial is an ArUCo square fiducial. In some embodiments, the fiducial is rigidly attached to an outward facing side of the neuroimaging device and centered along a base of the neuroimaging device.

It is appreciated that methods in accordance with the present disclosure can include any combination of the aspects and features described herein. That is, methods in accordance with the present disclosure are not limited to the combinations of aspects and features specifically described herein, but also may include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF THE DRAWINGS

A better understanding of the features and advantages of the present subject matter will be obtained by reference to the following detailed description that sets forth illustrative embodiments and the accompanying drawings of which:

FIGS. 3A and 4B depict example flow charts detailing the series of events and decisions that guide users to the correct device alignment and sufficient signal quality;

FIGS. 4A-4L depicts images and representative screenshots at various stages of the NACE process;

DETAILED DESCRIPTION

Figure 1A:
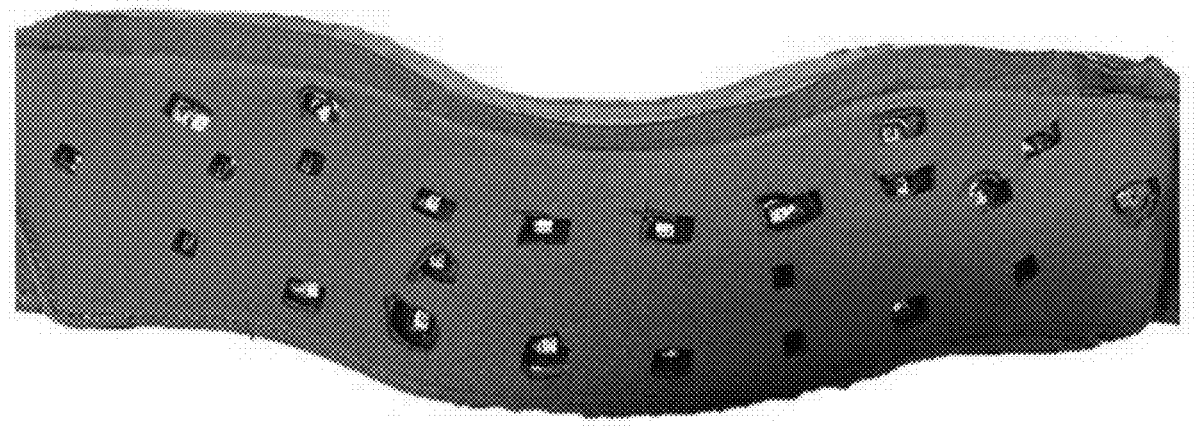
FIG. 1A depicts an example is of an fNIRS device.

Before any embodiments of the disclosure are explained in detail, it is to be understood that the disclosure is not limited in its application to the details of embodiment and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting, and coupling. Further, "connected" and "coupled" are not restricted to physical or mechanical connections or couplings, and can include electrical or hydraulic connections or couplings, whether direct or indirect.

Embodiments of the present disclosure are generally directed to NACE systems. These systems includes a neuroimaging device, a fiducial affixed to the neuroimaging device, an imaging device, and an AR module coupled to the imaging device. The AR module is configured to provide alignment data for the neuroimaging device by tracking facial or cranial landmarks and the fiducial.

Definitions

Unless otherwise defined, all technical terms used herein have the same meaning as commonly understood by one of ordinary skill in the art to which the present subject matter belongs. As used in this specification and the appended claims, the singular forms "a," "an," and "the" include plural references unless the context clearly dictates otherwise. Any reference to "or" herein is intended to encompass "and/or" unless otherwise stated.

As used herein, the term "real-time" refers to transmitting or processing data without intentional delay given the processing limitations of a system, the time required to accurately obtain data and images, and the rate of change of the data and images. In some examples, "real-time" is used to describe the presentation of information obtained from components of embodiments of the present disclosure.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. The term "approximately" as used herein refers to any values, including both integers and fractional components that are within a variation of up to $\pm 10\%$ of the value modified by the term "about." In certain aspects, the term "approximately" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "approximately" can mean within 3 or more than 3 standard deviations, per the practice in the art. Alternatively, such as with respect to biological systems or processes, the term "about" can mean within an order of magnitude, in some embodiments, within 5-fold, and in some embodiments, within 2-fold of a value.

Overview

A major strength of the described NACE system is that it enables users to easily set up neuroimaging devices using just a smartphone or tablet computer. Although previous systems display "target" positions for devices and can compute the resulting errors, the interactive guidance scheme from NACE that updates on-screen indications in response to the status of where objects are in physical space is beneficial for successful technology adoption.

Furthermore, in some embodiments, NACE automates the standard operating procedure for aligning neuroimaging devices, thereby enabling lay users to set up devices without expert support. This new capability makes it practical to achieve widespread adoption of naturalistic neuroimaging performed by lay users and, consequently, may enable neuroimaging researchers to collect the much larger volumes of data needed to achieve clinically meaningful results. Notably, the strategy underlying NACE could be extended to other neuroimaging modalities that have historically probe-like placement of sensors over the cranium (for ex. EEG) but are now being deployed in non-modular fashions to facilitate miniaturization, durability, and affordability.

Figure 1B:
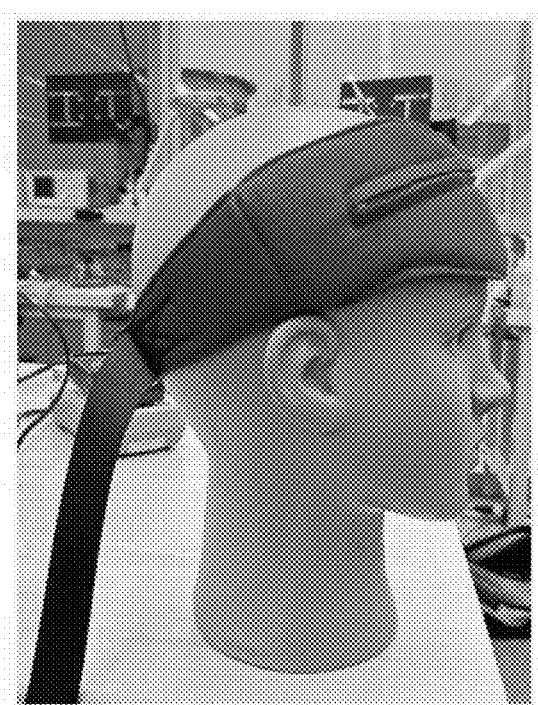
FIG. 1B depicts an example assembled device.
Figure 1C:
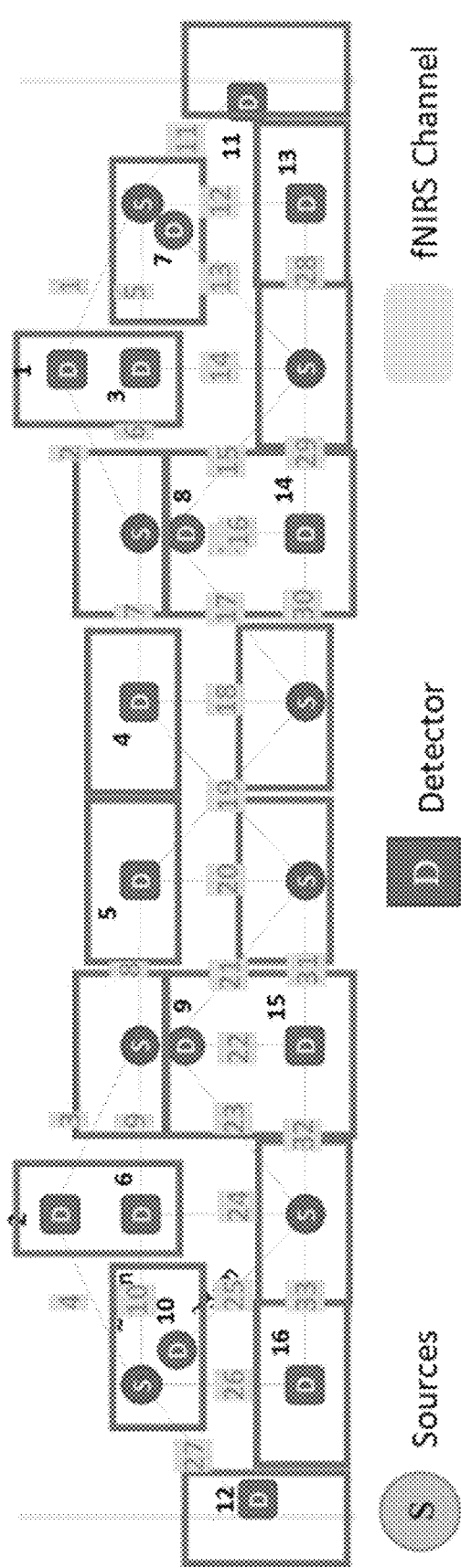
FIG. 1C depicts an example source-detector layout of custom fNIRS device.

In some embodiments, the fNIRS device used is a custom-designed headset of similar form factor to PFC-imaging devices designed by commercial vendors and research groups. In some embodiments, the device comprises eight LED light sources, emitting light at wavelengths of 740 nm and 850 nm, and 16 silicon-photodiode-based light detectors. In some embodiments, the layout of the sources and detectors results in a total of 33 long channels with a source-detector separation of 28 mm. In some embodiments, the device wirelessly transmits 10-Hz data via Bluetooth® to an Android® tablet application. FIG. 1 shows the channel layout and physical view of the fNIRS device. For ease and user comfort, in some embodiments, the rigid-flex printed circuit board (PCB) system holding the electronics components is enclosed in a silicone over-mold that makes soft, conformal contact with the user's forehead. In some embodiments, the silicone-electronics assembly is then pressed to the forehead using a conformal rigid visor with an adjustable Velcro® strap. In some embodiments, key to the device with NACE is placement of an ArUCo marker at a central location on the front of the device. In some embodiments, the marker is rigidly attached to the outward facing side centered along the base of the device.

Metrics for Evaluation

In some embodiments, correct positioning of the device is defined as placement at the 10% mark along the nasion-inion axis. To successfully guide a user to align a device, in some embodiments, the AR guidance application quantifies the vertical, lateral, and rotational offset of the device with respect of facial landmarks in real time. In some embodiments, the NACE algorithm assumes that the ArUCo marker has been place on the device such that, when positioned correctly, the base of the device coincides with the nasion-inion axis and the "FPZ" location defined as per the international 10-10 layout.

Figure 2:
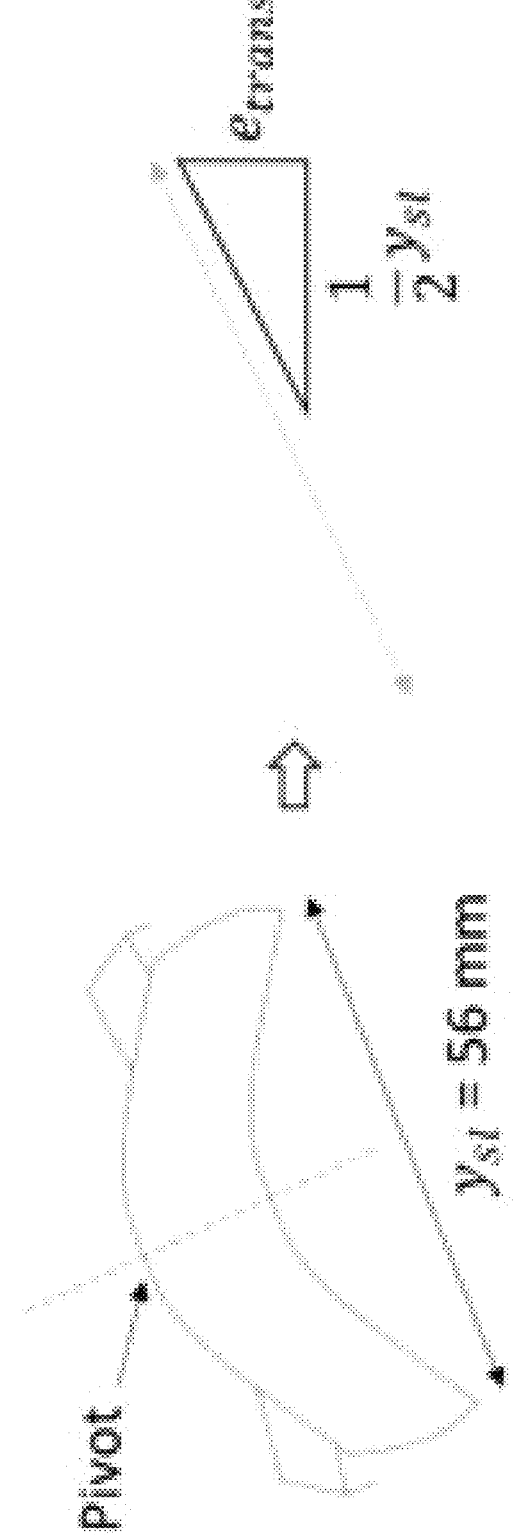
FIG. 2 depicts a calculation of maximum permitted rotation error using device length and maximum permitted translation error.

To estimate the necessary target alignment accuracy, in some embodiments, data from the Human Connectome Project (HCP) atlas, which provides a functional cortical parcellation of the human brain based on aggregating functional magnetic resonance imaging (fMRI) studies, is used. Parcel-wise surface area data were first calculated by dividing provided volumetric data (in mm3) by the maximum human cortical thickness of 5.5 mm36. Assuming each parcel was square shaped for ease of calculations, the minimum feature size was estimated by finding the square-root of the square parcels and found to be x_sfs=6.55 mm. Hence, as per the Nyquist theorem, the maximum permitted error in translational accuracy is e_trans=3.275 mm. The custom fNIRS headset shown in FIG. 1 has a sensor area length of 56 mm. If the device is assumed to be centered, and free to rotate along the center, achieving a 3.275 mm vertical tilt would require an e_rot of 2°. A graphic explaining this calculation and associated equation are shown in FIG. 2 and equation $$e_{rot} = \arctan\left(\frac{e_{trans}}{\frac{1}{2}y_{sl}}\right) = \arctan\left(\frac{3.3\,\text{mm}}{28\,\text{mm}}\right) = 2° \tag{1}$$

Algorithm Design

In some embodiments, NACE is implemented on Android® and incorporates a three-part process for user-specific app setup (Part 1), device alignment with respect to cranial landmarks (Part 2), and sensor scalp coupling evaluation (Part 3). In some embodiments, in Part 1, the researcher installs and sets up the application for a user with a one-time camera calibration and cranial measurements (e.g., data entry). In some embodiments, in Part 2, the app collects live video data from the "selfie" (front-facing) camera of a mobile device (e.g., tablet) and continually identifies cranial landmarks and the position of the neuroimaging device from streamed video frames. A simple user interface then provides AR cues overlaid on a mirrored camera view to help lay users shift and rotate the device to bring it into correct alignment with the correct cranial landmarks. In some embodiments, in Part 3, NACE collects data from a Bluetooth-enabled neuroimaging device, measures its signal quality, and presents a second user interface to guide when and where to tighten the device to enable optimal scalp coupling.

Figure 3A:
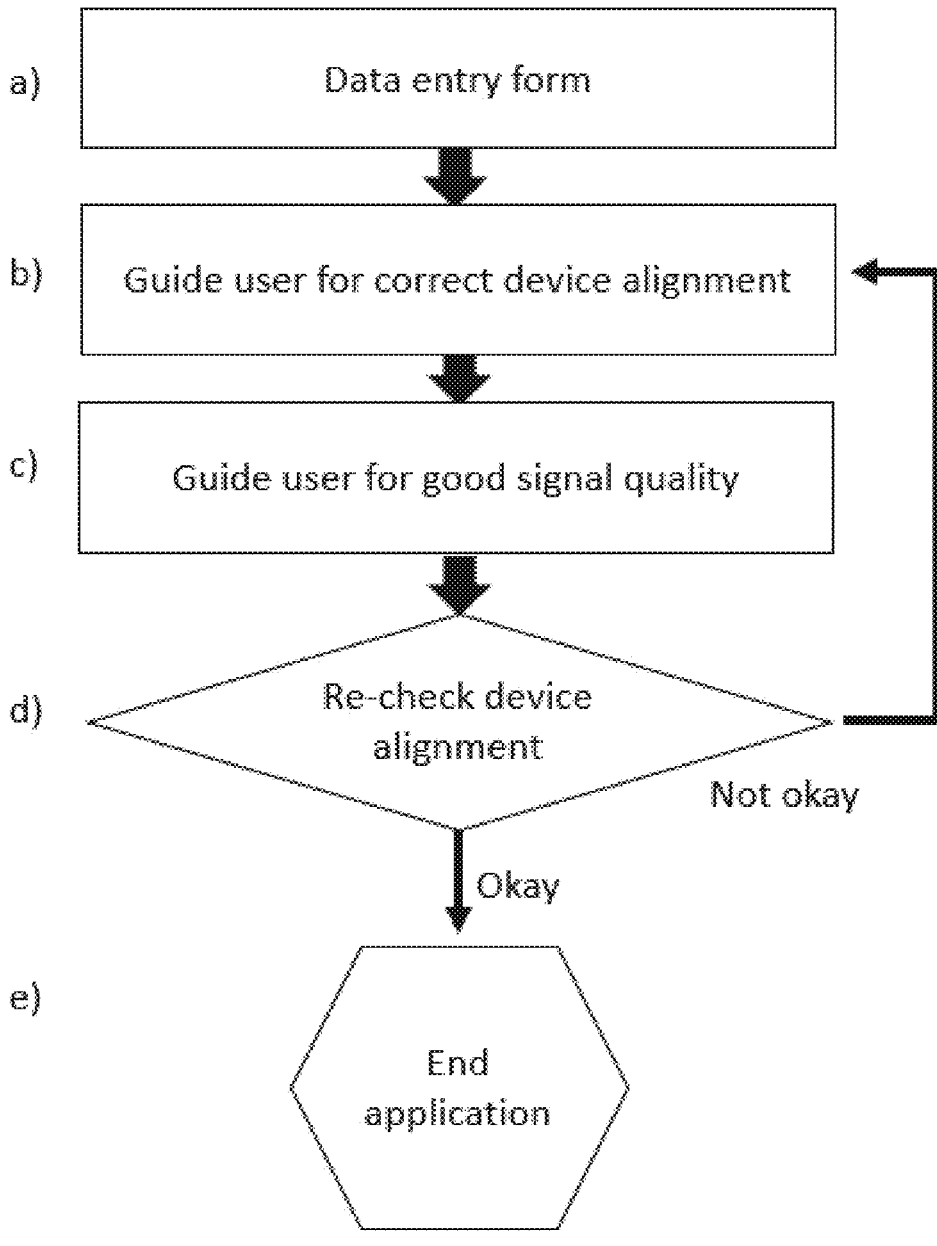

FIGS. 3A and 3B depicts the implementation of the NACE algorithm in a flowchart. The flowchart depicted in FIG. 3A shows an example embodiment of the overall flow of the application. Step a) The application presents a data entry form to intake cranial measurement data and Bluetooth® device selection. Step b) The application proceeds to interactively guide the user to align the headband to the correct location on the head. The application tracks the location of facial landmarks and fiducials built-in to the fNIRS headband to calculate and present both textual and graphical guidance cues to adjust the headband. Step c) The application proceeds to an interactive interface that streams fNIRS device data via Bluetooth®, evaluates the signal quality in real-time, and then presents the user guidance cues to tighten the headband or clear hair that may be blocking the array. Step d) The application proceeds to a quick re-check the alignment quality of the device. At this juncture, it either returns to the headband alignment interface, or it allows the user to proceed to step e) where the app will return to data collection.

The flowchart depicted in FIG. 3B shows an example embodiments of the algorithm for guiding the user for correct device alignment from FIG. 3A step c.

User-Specific App Setup (Steps 1.1 to 1.3)

In some embodiments, as a pre-requisite input, the app requires two inputs: 1) calibration data associated with the two-dimensional (2D) camera being utilized to remove barrel, pincushion, and mustache distortions from the raw image, and 2) cranial tape measurements of the nasion-inion distance ($d_{n2i}$), inter-eyebrow distance ($d_{ied}$), and the nasion-to-eyebrow-line ($d_{2el}$) distance. Both processes are only required once.

In some embodiments, camera calibration data is retrieved using an Android-based, open-sourced implementation of OpenCV's camera calibration software. In some embodiments, the calibration matrix is fed manually into the application codebase prior to application compiling. In some embodiments, this process is repeated for each unique device used and is performed when the application is installed on the mobile tablet.

In some embodiments, one-time cranial tape measurements are conducted by a skilled expert in lab environment before distributing the neuroimaging device and accompanying tablet for lay use. In some embodiments, data from the cranial measurement process is used by first launching the NACE application and recording values into the on-screen form. In some embodiments, once the required data are entered into the NACE application's opening page, the user can use the app with the input measurements anytime afterwards.

Figures 4A, 4B, 4C, 4D, 4E, 4F, 4G, 4H, 4I, 4J, 4K, 4L:
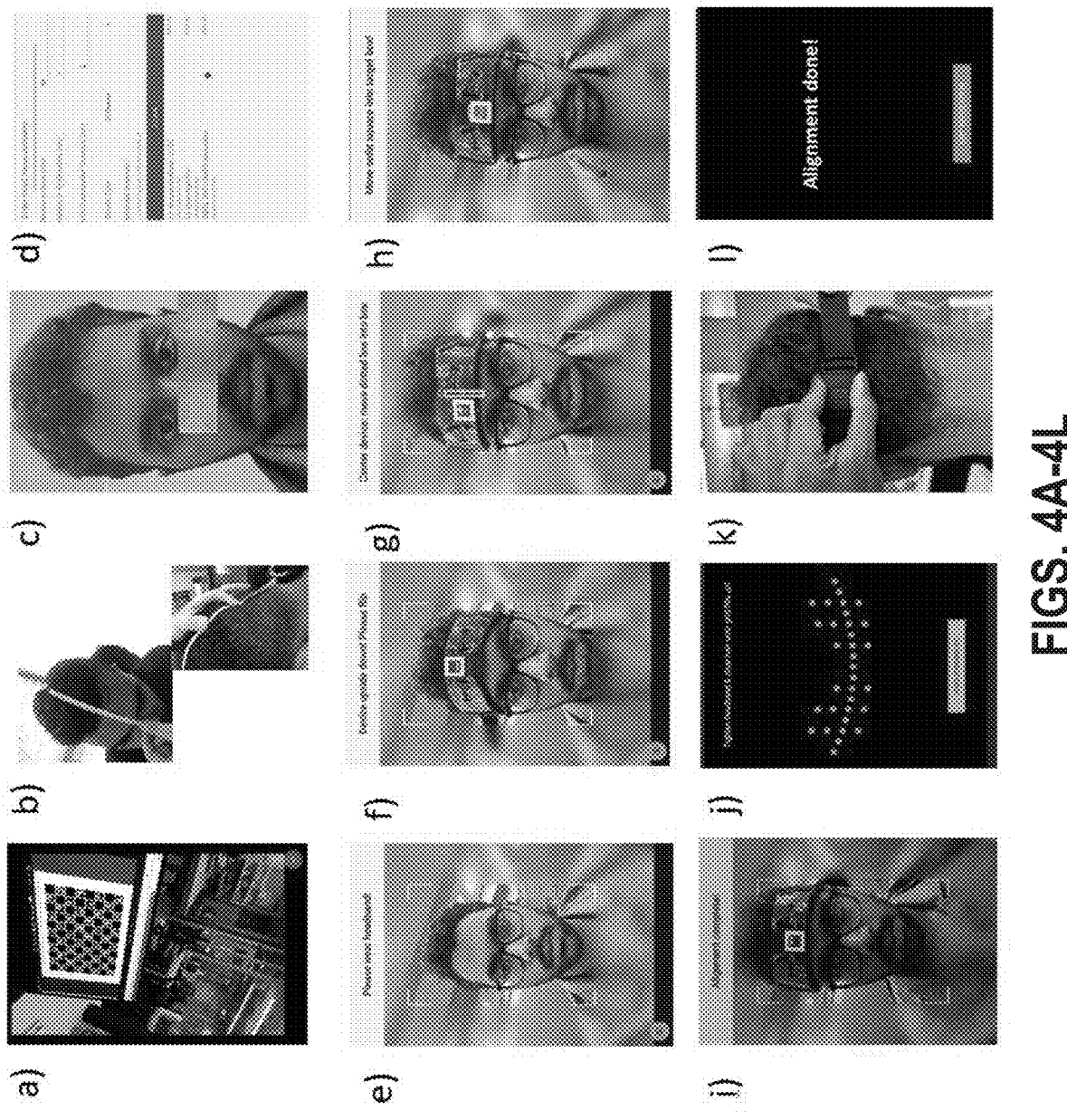

In some embodiments, when using the application (away from the researcher), the user switches on the custom device, and loads the application on the accompanying tablet. Although the tablet can be held in hand while using the application, in some embodiments, a dock is recommended while operating the device. In some embodiments, on the app opening page, the user presses the "Scan" button to start Bluetooth® Low Energy scanning and list out available devices nearby. In some embodiments, the user then selects a custom device titled "BBOL fNIRS Headband" from the listed options (FIG. 4D). In some embodiments, the application proceeds to the AR guidance screens.

Device Alignment (Steps 2.1 to 2.9):

FIGS. 4A-4L depicts images of preparatory setup and measurements for an embodiment of the application as well as screenshots of an embodiment of the application interface as experienced by the user. FIG. 4A depicts an image of a preparatory, one-time camera calibration to facilitate subsequent distortion correction by the application. FIG. 4B depicts an image of cranial measurements to identify the target location for alignment of the neuroimaging device. FIG. 4C depicts an image of the distance between the eyebrows or the "eyebrow line" that is measured for facilitating algorithm calculations. FIG. 4D depicts a screenshot of the application showing a data entry form wherein the user can enter the measurements collected and also select the device being utilized for the study. In some embodiments, as soon as the user selects the Bluetooth device from a list below the form, the application proceeds. FIG. 4E depicts an image showing that upon starting, the application requests user to wear headband. FIG. 4F depicts an image where, in case the user wears the headband upside down, they will be alerted. FIG. 4G depicts an image showing that the user is requested to center the device using graphical and textual cues. FIG. 4H depicts an image showing when a user is requested to shift the device marker into a target square using graphical and textual cues. FIG. 4I depicts an image showing that the user is alerted when the alignment of the device is complete. FIG. 4J depicts a screenshot showing that the user is then presented a grid of sensor locations mirroring the device placement on their forehead, and guided textually to tighten headband or clear hair over any channels that have insufficient signal quality. FIG. 4K depicts an image showing the user tightening headband in response to cues from previous step. FIG. 4L depicts a screenshot showing that the user is notified by the app that the alignment process is complete.

The general procedure for device alignment involves a set of initializations followed by an iterative process of extracting facial landmarks, verifying head and device position, and confirming that alignment is complete. In some embodiments, this section of the NACE application begins with presentation of the selfie camera view and begins searching and tracking for facial landmarks (using Google MLKit) and an ArUCo marker (using OpenCV) pre-attached to the device (FIG. 4A). In some embodiments, in case the ArUCo marker is not found, the user is instructed to wear the fNIRS headset.

In some embodiments, the tracked points for both are outlined on the user interface. In some embodiments, the orientation of the device is inferred from the orientation of the ArUCo marker; if the device is upside down, in some embodiments, the application notifies the user using a textual cue (FIG. 4E). In some embodiments, the application loops until the device is oriented uprightly.

In some embodiments, once the device is detected to be upright, textual, and graphical cues appear on screen to help the user orient their head correctly with respect to the camera. In some embodiments, textual cues are iteratively presented to guide the user to move close to the screen, look straight at the screen, and tilt their head gently forward to ensure that the ArUCo marker is parallel to the camera plane (FIGS. 4F through 4H).

In some embodiments, the device alignment process depends on two serialized sub-processes: 1) presentation of the device target location and 2) calculation of the current device location with respect to the cranial landmarks. Both processes depend on the user's head looking straight and being tilted forward parallel to the camera plane. This leverages the shape of the frontal bone (classified as a cranial "flat bone") to simplify pixel to distance measurements along the nasion-inion axis. In some embodiments, the software detects both aspects by simply comparing the lengths of the opposite pairs of the square ArUCo marker and requiring them all to be 95% equal in pixel count.

Once the software detects that the head is tilted forward to be parallel to the camera plane, in some embodiments, a square target is rendered over the real-time camera feed of the user face (FIG. 4D). In some embodiments, the square target is drawn in a manner that the center of its base coincides with the "FPZ" landmark of the 10-10 layout. In some embodiments, the "FPZ" point is located with respect to the center of the eyebrow-line.

Figure 5A:
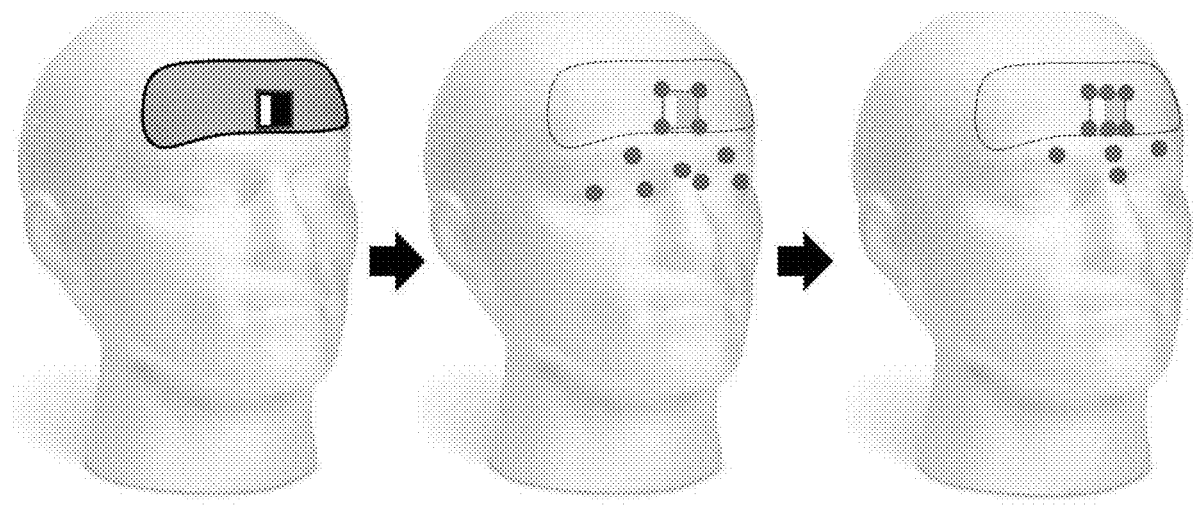
FIGS. 5A-5E show and example approach to quantify the rotational and translational alignment error used for subsequent alignment quality check.
Figure 5B:
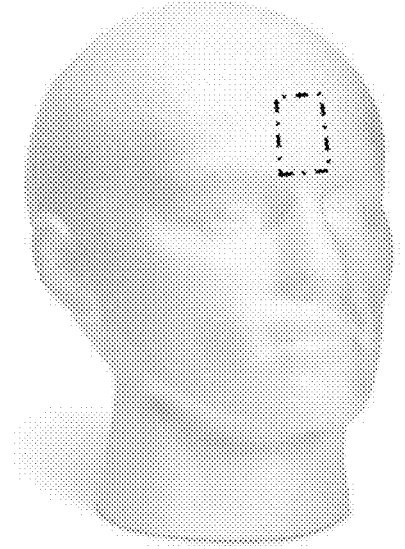
Figure 5C:
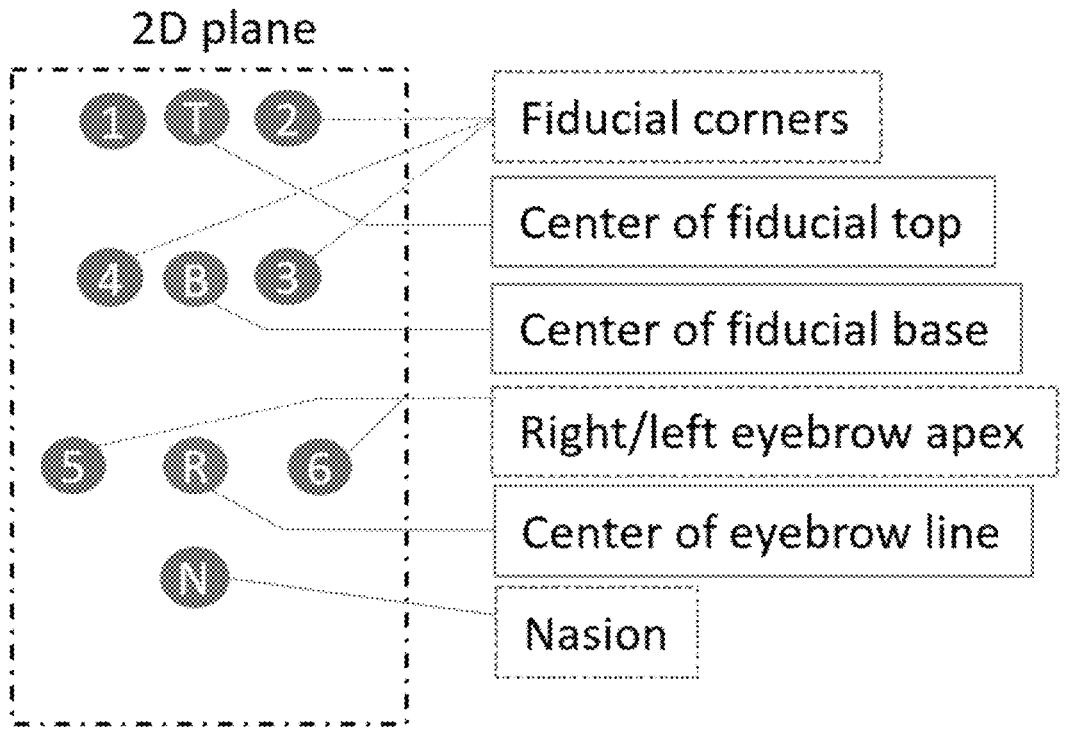
Figure 5D:
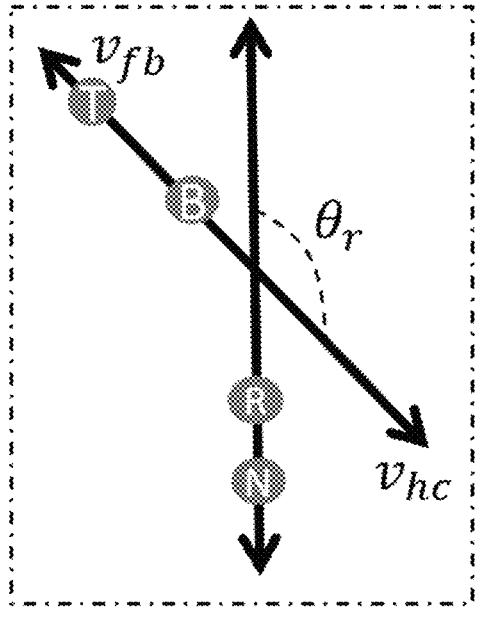
Figure 5E:
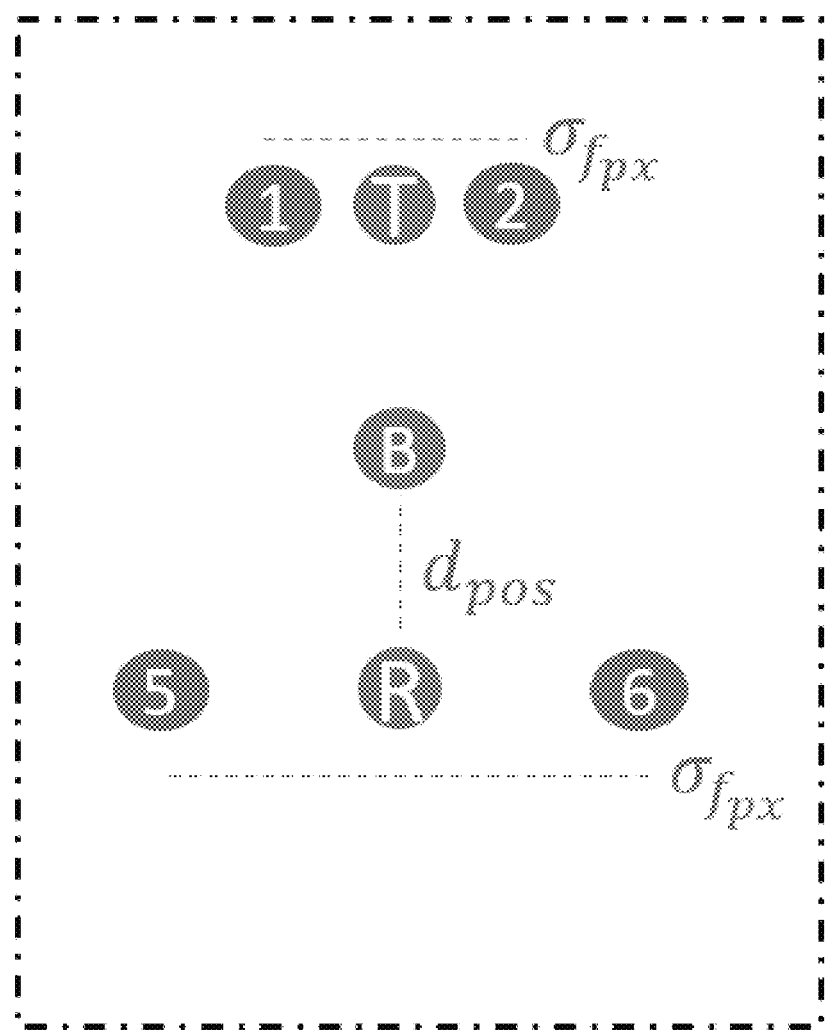

FIGS. 5A-5E show and example approach to quantify the rotational and translational alignment error used for subsequent alignment quality check. FIG. 5A depicts landmarks and a fiducial on the fNIRS device are tracked (middle) and used to infer a handful of points (right). Green represents points tracked directly using Google MLKit technology and OpenCV, and magenta represents center points calculated by simple averaging. FIG. 5B shows that the algorithm simplifies 3D positioning on the head by reducing the problem to a 2D cartesian mathematics problem. In some embodiments, this approach leverages the center forehead bone being characterized as a 'flat' bone. FIG. 5C depicts the specific points on the face and device are further detailed and labeled for subsequent description. FIG. 5D depicts the angle of the device rotation with respect to the face ($\theta_r$) is calculated between the vectors formed by the fiducial base ($v_{fb}$) and the centerline of the face ($v_{hc}$) formed by the center of the eyebrow line point 'R' and the nasion point 'N'. FIG. 5E depicts the distance of the fiducial base and the eyebrow line is calculated using the equation $$\left(\frac{abs\,(\sigma_{ebl} - \sigma_{ft})}{d_{TR_{px}}}\right)\!(d_{BR_{px}})$$

that linearly models the changes in pixel density (millimeters/pixels) from the eyebrow line to the top of the fiducial line. The pixel densities are calculated by dividing data entered in a form by the pixel distances measured between the respective points.

In some embodiments, the system employs a strategy to calculate the target position. In some embodiments, the target drawing process works by leveraging 1) a subset of facial landmarks on the eyebrows (left/right centers) and 2) the inter-eyebrow-center measurement collected earlier during one-time cranial measurements. In some embodiments, the inter-eyebrow distance is first tracked in pixels ($l_{ied}$) and the pixel density at the eyebrow-line ($\rho_{el}$), or the number of millimeters per pixel in the forehead region, are calculated by dividing $l_{ied}$ by $d_{ied}$. Following this, in some embodiments, the center point of the eyebrow-line is identified using the left and right eyebrow centers ($p_{EB_{Left}}$, $p_{EB_{Right}}$) tracked by Google MLKit, and the "FPZ" location is identified by simply converting the desired distance between "FPZ" and the eyebrow-line center to pixels using ($\rho_{el}$). Equations to find "FPZ" arriving at this calculation are shown in equation 2:

$$p_{FPZ}\langle x, y\rangle = \left\langle \frac{1}{2}\left(p_{EB_{Left_x}} + p_{EB_{Right_x}}\right), \right.$$
$$\left. \frac{1}{2}\left(p_{EB_{Left_y}} + p_{EB_{Right_y}}\right) + \frac{1}{10}(d_{n2i}) - d_{n2el}\right)\left(\frac{1}{\rho_{el}}\right)\right\rangle \quad (2)$$

With the target position now identified, in some embodiments, on-screen instructions guide the user to move the square ArUCo fiducial on the device (outlined with tracking dots) to within the bounds of the target. After the target is presented, in some embodiments, the NACE application begins calculating the translational and rotational offset between the base of the device's ArUCo marker and the center of the eyebrow-line ($p_{EB_{center}}$). In some embodiments, the center of the bottom edge of the ArUCo marker ($p_{fbc}$) and the tracked location of the eyebrow line are used to calculate a vector $\vec{a}$. In some embodiments, the displacement of this vector is calculated using the pixel Euclidean distance between $p_1$ and $p_2$. In some embodiments, the rotation of the vector is calculated with respect to a vector $\vec{b}$ between the center of the eyeline and eyebrow line. In some embodiments, the vector displacement is converted using a pixel density calculated by dividing the pixel length of the ArUCo marker by its metric length known a priori. To be considered aligned, in some embodiments, the device needs to be at the 10% mark along the nasion-inion axis. However, a tolerance of 3.3 mm for displacement and 2° for rotation have been granted as per prior calculations discussed earlier.

$$p_{EB_{center}} = \text{center of eyebrow line}$$

-continued $$p_{EB_{Left,Right}} = \text{left and right eyebrow}$$

$$p_{Eye_{Left,Right}} = \text{left and right eyes}$$

$$p_{Eye_{Center}} = \text{center of eyes}$$

$$d_{interSOR} = \text{inter–supra orbital ridge measurement (mm)}$$

$$p_{fbc} = \text{center of fiducial base}$$

$$p_{fB_{left}}, p_{fB_{right}} = \text{bottom corners of } ArUCo \text{ fiducial base}$$

$$\vec{a} = \text{vector of fiducial base}$$

$$\vec{b} = \text{vector between center of } SOR \text{ and center of eyeline}$$

$$\vec{c} = \text{vector between center of } SOR \text{ and center of fiducial base}$$

$$\theta_r = \text{device rotation} = \qquad (3)$$
$$\tan^{-1}\!\left(\frac{p_{fB_{left}y} - p_{fB_{right}y}}{p_{fB_{left}x} - p_{fB_{right}x}}\right) - \tan^{-1}\!\left(\frac{p_{Eye_{left}y} - p_{Eye_{right}y}}{p_{Eye_{left}x} - p_{Eye_{right}x}}\right)$$

$$\theta_t = \text{translation vector angle} = \qquad (4)$$
$$\tan^{-1}\!\left(\frac{p_{fbc_y} - p_{Eye_{Center_y}}}{p_{fbc_x} - p_{Eye_{Center_x}}}\right) - \tan^{-1}\!\left(\frac{p_{EB_{center_y}} - p_{Eye_{Center_y}}}{p_{EB_{center_x}} - p_{Eye_{Center_x}}}\right)$$

$$d = \sqrt{\left(p_{fbc_x} - p_{EB_{center_x}}\right)^2 + \left(p_{fbc_y} - p_{EB_{center_y}}\right)^2} \qquad (5)$$
$$\left(\frac{d_{interSOR}}{\sqrt{(p_{sorLeftx} - p_{sorRightx})^2 + (p_{sorLefty} - p_{sorRighty})^2}}\right)$$

Once alignment is complete, in some embodiments, the user progresses to check for good sensor coupling.

Sensor Coupling (Steps 3.1 to 3.7)

In some embodiments, the general procedure to assess sensor coupling involves iterative measurement of the signal-to-noise ratio (SNR) associated with real-time, Bluetooth data from each channel. In some embodiments, SNR is calculated as $$SNR = 20\log_{10}\left(\frac{\mu}{\sigma}\right),$$

where $\mu$ is the DC offset of the raw photodiode voltage and $\sigma$ represents the signal variance over the sampling duration. In some embodiments, the SNR threshold for acceptable signal quality was set to 20 dB for every channel in accordance with the "Best practices for fNIRS publications" manuscript.

In this manuscript, poor signal quality is assumed as due to poor scalp-sensor coupling. In some embodiments, the main source of poor scalp-sensor coupling in the device used in this work is lack of direct contact between the neuroimaging and the scalp. Thus, in some embodiments, the goal of the sensor coupling steps are to determine which channels do not show acceptable signal quality and to instruct the user to tighten the device accordingly. To assist the user with identifying which channels need adjusting for, in some embodiments, NACE presents a layout representing the device shape and colors the individual sensor locations to indicate if sensor quality is sufficient.

The user interface of the application during the signal quality evaluation window is shown in FIG. 4J. A mock outline of the device is presented on-screen with four rhombi for each quadrant of the sensor area. In some embodiments, the entire system can be tightened using one strap placed at the rear of the device (FIG. 4K). In some embodiments, the algorithm continually calculates the SNR of each channel and presents the circles as empty or filled, depending on the SNR meeting or exceeding the 20 dB threshold. In some embodiments, channels towards the lateral ends of the device are not required to be complete since they only require fNIRS.

Algorithm Evaluation

IRB-approved human subject testing of the NACE system was conducted to evaluate the positioning accuracy, device signal quality, and setup duration the AR algorithm enables for lay users with respect to independent and expert-provided setup of the device.

For positioning accuracy evaluation, a Pollhemus Patriot digitizer system was utilized for its high static resolution (1.524 mm) and well documented deployment for neuroimaging applications.

A total of 10 subjects were recruited for three different sets of tasks: 1) device setup quality without AR algorithm, 2) device setup quality with skilled expert, and 3) device setup quality with AR algorithm. Each set of tasks is described below, and all data was recorded using RedCap.

The first task aimed to measure the positioning accuracy, device signal quality, and setup duration when a research expert performs the device placement. For this task, subjects were requested to sit in place while an "expert" user (member of our lab) positioned the fNIRS headset on the user forehead using a tape measure. After one practice round, three device placement rounds were performed. After each device placement the four corners of the attached ArUCo marker fiducial were digitally mapped using the digitizer. The time taken by each of the three repetitions was also recorded, and the timer was started from each moment the expert began taking cranial measurements of the user for device placement.

The second task aimed to measure the positioning accuracy, device signal quality, and setup duration when a lay user independently placed the device without the presence of an expert of the AR guidance application. For this task, subjects were requested to place the fNIRS device independently on their forehead without using NACE. They were verbally instructed to independently 1) align the fNIRS headset in a symmetrical manner along the 10% mark of the nasion-inion axis using a handheld mirror and tape measure (10% of the nasion-inion axis). They were given one practice round followed by three device placement rounds, and after each round the four corners of the ArUCo marker fiducial on the device was digitally mapped using the digitizer. The error measurement process constitutes measurement of the translational error (mm) and rotational error (degrees) with respect to the "correct" distance and rotation along the nasion-inion axis. The time taken by each of the three repetitions was also recorded, and the timer was started from each moment the lay user began taking cranial measurements of the user for device placement.

For the third and final task, subjects were requested to utilize the AR guidance application to position the headset independently. After each device placement the four corners of the attached ArUCo marker fiducial were digitally mapped using the digitizer. The time taken by each of the three repetitions was automatically logged by the AR guidance application and saved in a local application data file along with other tracking and fNIRS data for future analysis.

Results and Discussion

Figure 6A:
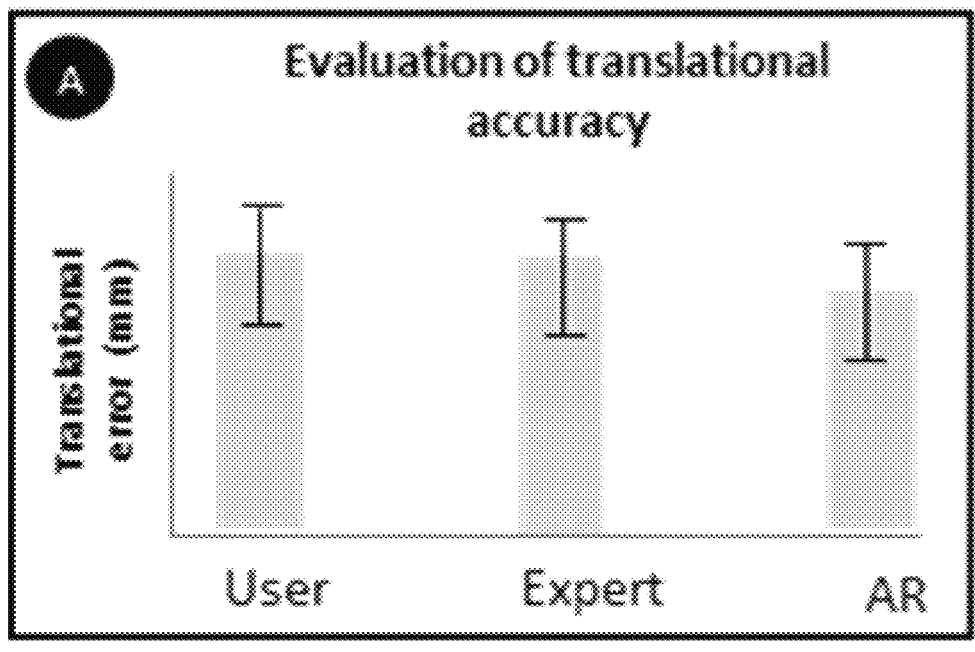
FIG. 6A depicts a chart showing translational positioning error by task group.
Figure 6B:
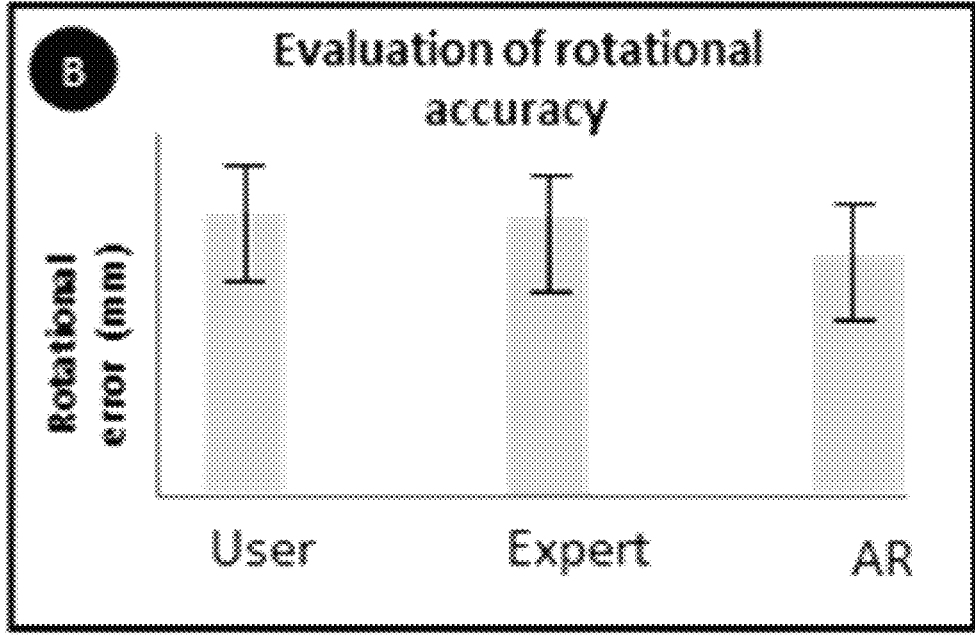
FIG. 6B depicts a chart showing rotational positioning error by task group.
Figure 6C:
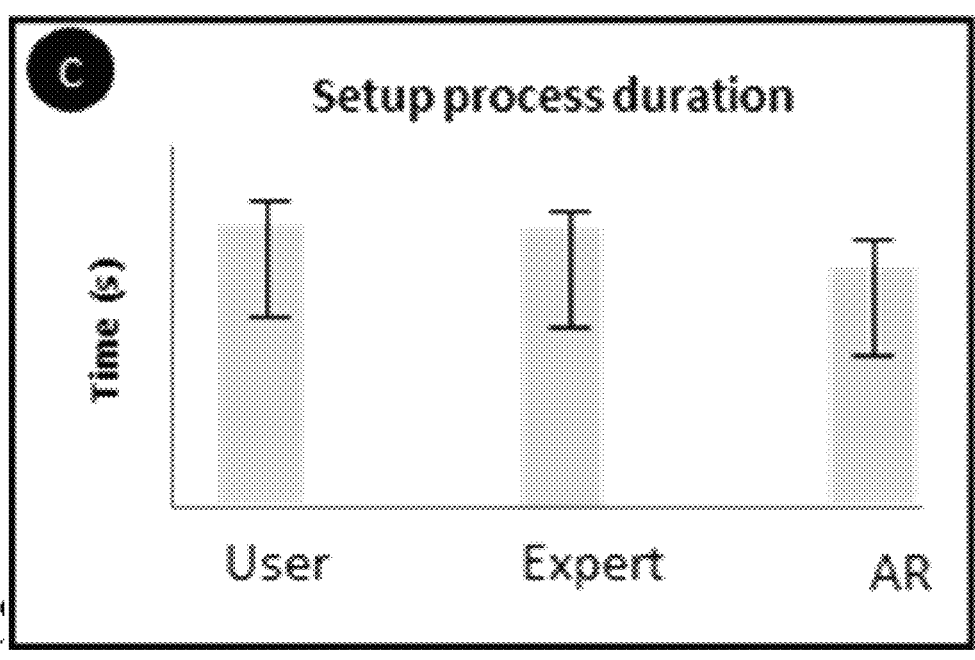
FIG. 6C depicts a chart showing setup duration by task group.
Figure 6D:
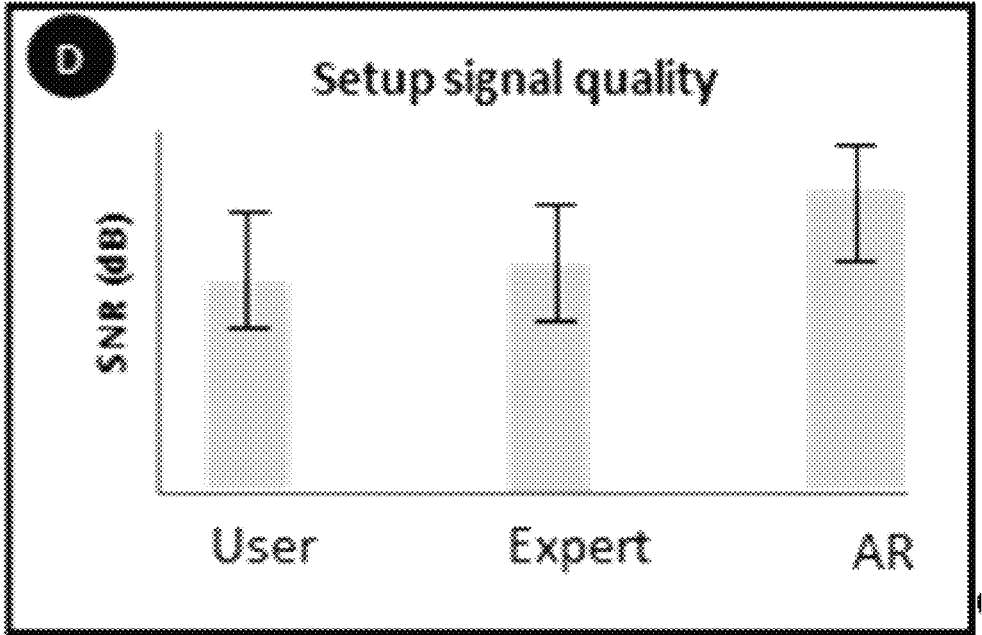
FIG. 6D depicts a chart showing a comparison of final setup signal quality by task group.

The human subject testing process aimed to assess the placement accuracy, repeatability, and time advantage the augmented reality application provides in comparison to independent placement of the device by lay users and expert placement on user heads. Error values recorded were measured manually using a flexible tape measure and protractor as detailed in the methods above and indicate the translational and rotational offset between the "FPZ" location and the placed location of the device. As shown in FIG. 6A and FIG. 6B, the translational and rotational error by lay users with AR guidance were well below the error thresholds, shown with the horizontal line, and commensurate to expert performance for device placement. Both translational and rotational error were beyond permissible thresholds for device placement errors. The repeatability of the alignment process was measured by recording the difference in absolute error values between successive device placements. As shown in FIG. 6C, device placement times dropped drastically by using the AR guidance application. Compared to the several minutes required by independent and expert users to place the headset, the AR guidance enabled headset placement within a matter of seconds. Finally, as shown in FIG. 6D, the SNR measurement after device placement for users utilizing the AR application was found to be comparable to the device placement by the expert or independently without the AR application. These results demonstrate that the NACE technology provides accurate and repeatable device positioning along with guiding users towards better device signal quality.

Example System

Figure 7:
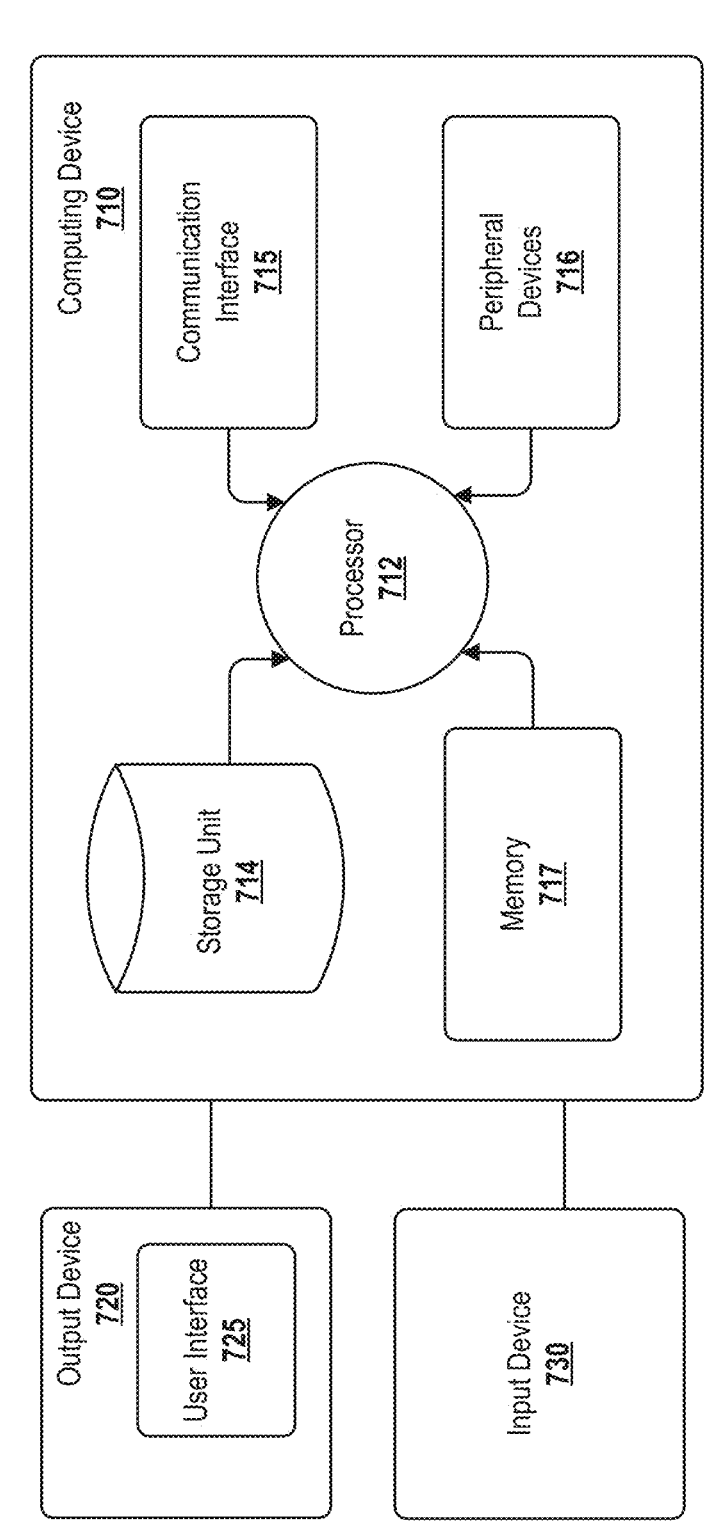
FIG. 7 depicts an example system that includes a computer or computing device that can be programmed or otherwise configured to implement systems or methods of the present disclosure.

FIG. 7 depicts an example system 700 that includes a computer or computing device 710 that can be programmed or otherwise configured to implement systems or methods of the present disclosure. In the depicted embodiment, the computer or computing device 710 includes an electronic processor (also "processor" and "computer processor" herein) 712, which is optionally a single core, a multi core processor, or a plurality of processors for parallel processing. The depicted embodiment also includes memory 717 (e.g., random-access memory, read-only memory, flash memory), electronic storage unit 714 (e.g., hard disk or flash), communication interface 715 (e.g., a network adapter or modem) for communicating with one or more other systems, and peripheral devices 716, such as cache, other memory, data storage, microphones, speakers, etc. In some embodiments, the memory 717, storage unit 714, communication interface 715 and peripheral devices 716 are in communication with the electronic processor 712 through a communication bus (shown as solid lines), such as a motherboard. In some embodiments, the bus of the computing device 710 includes multiple buses. In some embodiments, the computing device 710 includes more or fewer components than those illustrated in FIG. 7 and performs functions other than those described herein.

In some embodiments, the memory 717 and storage unit 714 include one or more physical apparatuses used to store data or programs on a temporary or permanent basis. In some embodiments, the memory 717 is volatile memory and requires power to maintain stored information. In some embodiments, the storage unit 714 is non-volatile memory and retains stored information when the computer is not powered. In further embodiments, memory 717 or storage unit 714 is a combination of devices such as those disclosed herein. In some embodiments, memory 717 or storage unit 714 is distributed across multiple machines such as a network-based memory or memory in multiple machines performing the operations of the computing device 710.

In some cases, the storage unit 714 is a data storage unit or data store for storing data. In some instances, the storage unit 714 store files, such as drivers, libraries, and saved programs. In some embodiments, the storage unit 714 stores user data (e.g., user preferences and user programs). In some embodiments, the computing device 710 includes one or more additional data storage units that are external, such as located on a remote server that is in communication through an intranet or the internet.

In some embodiments, methods as described herein are implemented by way of machine or computer executable code stored on an electronic storage location of the computing device 710, such as, for example, on the memory 717 or the storage unit 714. In some embodiments, the electronic processor 712 is configured to execute the code. In some embodiments, the machine executable or machine-readable code is provided in the form of software. In some examples, during use, the code is executed by the electronic processor 712. In some cases, the code is retrieved from the storage unit 714 and stored on the memory 717 for ready access by the electronic processor 712. In some situations, the storage unit 714 is precluded, and machine-executable instructions are stored on the memory 717.

Examples of operations performed by the electronic processor 712 can include fetch, decode, execute, and write back. In some cases, the electronic processor 712 is a component of a circuit, such as an integrated circuit. One or more other components of the computing device 710 can be optionally included in the circuit. In some cases, the circuit is an application specific integrated circuit (ASIC) or a field programmable gate arrays (FPGAs). In some cases, the operations of the electronic processor 712 can be distributed across multiple machines (where individual machines can have one or more processors) that can be coupled directly or across a network.

In some cases, the computing device 710 is optionally operatively coupled to a communication network via the communication interface 715. In some cases, the computing device 710 communicates with one or more remote computer systems through the network. In some cases, a user can access the computing device 710 via the network. In some cases, the computing device 710 is configured as a node within a peer-to-peer network.

In some cases, the computing device 710 includes or is in communication with one or more output devices 720. In some cases, the output device 720 includes a display to send visual information to a user. In some cases, the output device 720 is a liquid crystal display (LCD). In other cases, the output device 720 is a thin film transistor liquid crystal display (TFT-LCD) or an organic light emitting diode (OLED) display. In some cases, the output device 720 is a touch sensitive display that combines a display with a touch sensitive element that is operable to sense touch inputs as and functions as both the output device 720 and the input device 730. In still further cases, the output device 720 is a combination of devices such as those disclosed herein. In some cases, the output device 720 displays a user interface (UI) 725 generated by the computing device (for example, software executed by the computing device 710).

In some cases, the computing device 710 includes or is in communication with one or more input devices 730 that are configured to receive information from a user. In some cases, the input device 730 is a keyboard. In some cases, the input device 730 is a keypad (e.g., a telephone-based keypad). In some cases, the input device 730 is a cursor-control device including, by way of non-limiting examples, a mouse, trackball, track pad, joystick, game controller, or stylus. In some cases, as described above, the input device 730 is a touchscreen or a multi-touchscreen. In other cases, the input device 730 is a microphone to capture voice or other sound input. In other cases, the input device 730 is a camera or video camera. In still further cases, the input device is a combination of devices such as those disclosed herein.

In some cases, the computing device 710 includes an operating system configured to perform executable instructions. The operating system is, for example, software, including programs and data that manages the device's hardware and provides services for execution of applications.

As used herein, the term "module" may refer to a collection of one or more logic elements that, together, perform one or more functions associated with the module. Different ones of the logic elements in a module may take the same form or may take different forms. For example, some logic in a module may be implemented by a programmed general-purpose processing device, while other logic in a module may be implemented by an ASIC. In another example, different ones of the logic elements in a module may be associated with different sets of instructions executed by one or more processing devices. A module may not include all of the logic elements depicted in the associated drawing; for example, a module may include a subset of the logic elements depicted in the associated drawing when that module is to perform a subset of the operations discussed herein with reference to that module.

It should also be noted that a plurality of hardware and software-based devices, as well as a plurality of different structural components may be used to implement the described examples. In addition, embodiments may include hardware, software, and electronic components or modules that, for purposes of discussion, may be illustrated and described as if most of the components were implemented solely in hardware. In some embodiments, the electronic based aspects of the disclosure may be implemented in software (e.g., stored on non-transitory computer-readable medium) executable by one or more processors, such as electronic processor 712. As such, it should be noted that a plurality of hardware and software-based devices, as well as a plurality of different structural components may be employed to implement various embodiments. It should also be understood that although certain drawings illustrate hardware and software located within particular devices, these depictions are for illustrative purposes only. In some embodiments, the illustrated components may be combined or divided into separate software, firmware, or hardware. For example, instead of being located within and performed by a single electronic processor, logic and processing may be distributed among multiple electronic processors. Regardless of how they are combined or divided, hardware and software components may be located on the same computing device or may be distributed among different computing devices connected by one or more networks or other suitable communication links.

While preferred embodiments of the present disclosure have been shown and described herein, it will be obvious to those skilled in the art that such embodiments are provided by way of example only. Numerous variations, changes, and substitutions will now occur to those skilled in the art without departing from the described system. It should be understood that various alternatives to the embodiments described herein may be employed in practicing the described system.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Moreover, the separation or integration of various system modules and components in the implementations described earlier should not be understood as requiring such separation or integration in all implementations, and it should be understood that the described components and systems can generally be integrated together in a single product or packaged into multiple products. Accordingly, the earlier description of example embodiments does not define or constrain this disclosure. Other changes, substitutions, and alterations are also possible without departing from the spirit and scope of this disclosure.

What is claimed is:

1. A neuroimager alignment and coupling evaluation (NACE) system, comprising:
   a neuroimaging device configured to be removably coupled to a user's head, the neuroimaging device including a plurality of illumination sources and a plurality of light detectors positioned on an inside surface of the neuroimaging device;
   a fiducial coupled to an outside surface of the neuroimaging device;
   a portable imaging device operated by the user to acquire video of the neuroimaging device and the fiducial while on the user's head; and
   an augmented reality (AR) module in communication with the portable imaging device to receive the video, the AR module configured to present instructions to the user on the portable imaging device for aligning the neuroimaging device by tracking facial or cranial landmarks associated with the user's head relative to the fiducial in the video,
   wherein the neuroimaging device is a near-infrared spectroscopy (NIRS) device.

2. The system of claim 1, wherein the AR module is configured to:

process the video to identify the cranial landmarks and the position of the neuroimaging device.

3. The system of claim 1, wherein the portable imaging device includes a user interface, wherein the AR module is configured to provide the instructions to the user interface for display.

4. The system of claim 3, wherein the instructions include AR cues overlaid on a mirrored camera view.

5. The system of claim 3, wherein the instructions quantify the vertical, lateral, or rotational offset of the neuroimaging device with respect of the cranial landmarks.

6. The system of claim 3, wherein the AR module is configured to:
   receive signal data from the neuroimaging device;
   determine a measurement of a quality of the signal data; and
   provide the measurement of the quality of the signal data to the user interface.

7. The system of claim 1, wherein the neuroimaging device is a functional near-infrared spectroscopy (fNIRS) device.

8. The system of claim 1, wherein the neuroimaging device is configured to image the prefrontal cortex (PFC) region of the user's brain.

9. The system of claim 1, wherein the neuroimaging device is Bluetooth-enabled.

10. The system of claim 1, wherein the portable imaging device comprises a camera embedded in a mobile device.

11. The system of claim 1, wherein the fiducial is an ArUCo square fiducial.

12. The system of claim 1, wherein the fiducial is rigidly attached to an outward facing side of the neuroimaging device and centered along a base of the neuroimaging device.

13. The system of claim 1, wherein the instructions include adjustments to the neuroimaging device on the user's head.

14. The system of claim 1, wherein the instructions include textual cues and graphical cues to adjust the neuroimaging device on the user's head for alignment with the facial or cranial landmarks associated with the user's head.

* * * * *